(12) United States Patent
Brenan et al.

(10) Patent No.: US 9,180,459 B2
(45) Date of Patent: Nov. 10, 2015

(54) DEVICES AND METHODS FOR THERMALLY-MEDIATED CHEMICAL REACTIONS

(75) Inventors: Colin J. H. Brenan, Marblehead, MA (US); Thomas B. Morrison, Winchester, MA (US); Tanya S. Kanigan, Winchester, MA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 1355 days.

(21) Appl. No.: 12/921,144

(22) PCT Filed: Mar. 6, 2009

(86) PCT No.: PCT/US2009/036324
§ 371 (c)(1),
(2), (4) Date: Mar. 2, 2011

(87) PCT Pub. No.: WO2009/111696
PCT Pub. Date: Sep. 11, 2009

(65) Prior Publication Data
US 2011/0152108 A1    Jun. 23, 2011

Related U.S. Application Data

(60) Provisional application No. 61/034,321, filed on Mar. 6, 2008.

(51) Int. Cl.
*C40B 60/00* (2006.01)
*B01L 7/00* (2006.01)
*B01L 3/00* (2006.01)

(52) U.S. Cl.
CPC ............... *B01L 7/52* (2013.01); *B01L 3/50851* (2013.01); *B01L 3/5027* (2013.01); *B01L 3/50857* (2013.01); *B01L 2300/0819* (2013.01); *B01L 2300/0877* (2013.01); *B01L 2300/185* (2013.01); *B01L 2300/1827* (2013.01); *B01L 2300/1833* (2013.01); *B01L 2300/1844* (2013.01)

(58) Field of Classification Search
None
See application file for complete search history.

(56) References Cited

U.S. PATENT DOCUMENTS

| | | | |
|---|---|---|---|
| 5,415,839 A | | 5/1995 | Zaun et al. |
| 5,746,982 A | * | 5/1998 | Saneii et al. ................... 422/134 |
| 2003/0113713 A1 | | 6/2003 | Glezer et al. |
| 2003/0155344 A1 | | 8/2003 | Cobb |
| 2004/0208792 A1 | | 10/2004 | Linton et al. |
| 2006/0094108 A1 | * | 5/2006 | Yoder et al. ................. 435/287.2 |
| 2009/0326279 A1 | * | 12/2009 | Tonkovich et al. ........... 568/487 |

OTHER PUBLICATIONS

PCT/US2009/036324, "International Search Report mailed Jun. 30, 2009", 4 Pgs.

* cited by examiner

*Primary Examiner* — Christopher M Gross

(57) ABSTRACT

One aspect of the invention provides container for thermal cycling a plurality of samples in a microfluidic array. The container includes a plurality of walls defining an interior volume and a conductive member for heating the interior volume. Another aspect of the invention provides container for thermal cycling a plurality of samples in a microfluidic array. The container includes a plurality of walls defining an interior volume and a plurality of conductive members for heating an interior volume. Another aspect of the invention provides a container for thermal cycling a plurality of samples in a microfluidic array. The container includes a plurality of walls defining an interior volume and a first conductive member located in the interior volume and adapted to contact a first end of the microfluidic array.

14 Claims, 15 Drawing Sheets

DEVICES AND METHODS FOR THERMALLY-MEDIATED CHEMICAL REACTIONS

CROSS REFERENCES TO RELATED APPLICATIONS

This application claims priority to U.S. Provisional Patent Application Ser. No. 61/034,321, filed Mar. 6, 2008. The contents of this patent application are hereby incorporated by reference in their entirety.

TECHNICAL FIELD

New apparatus and methods for thermal cycling specimens are provided herein. The methods are applicable to specimens held in a variety of laboratory vessels and are particularly advantageous when used in conjunction with specimens held in a through-hole array.

BACKGROUND

Various research and diagnostic techniques employ thermally-mediated chemical reactions such as the polymerase chain reaction (PCR), nucleic acid hybridization, and protein immunoassays and/or thermally-controlled environments for cell culture. Such techniques utilize a thermal cycler (also known as a thermocycler, PCR machine, and/or DNA amplifier). Thermal cyclers provide the high temperatures necessary to physically separate the strands of DNA double helix that is used as a template at lower temperatures for DNA synthesis by a DNA polymerase (e.g. Taq polymerase) to selectively amplify the target DNA.

Current methods for changing temperature of a liquid contained in a microtiter plate or sealed tube (e.g. Eppendorf tube or capillary tube) make use of an external, temperature-controlled liquid or solid to transfer heat into or extract heat from the liquid PCR reagents in an enclosed container. The primary limitation of this approach is the requirement for an intervening material between the energy source and the heated or cooled liquid. Miniaturization and scaling to larger numbers of liquid volumes to be heated and cooled is particularly problematic with the current art because of the dual design constraints of having to seal and heat/cool a large volumes of liquids contained in the well of a thermoplastic microtiter well plate.

SUMMARY OF THE INVENTION

One aspect of the invention provides container for thermal cycling a plurality of samples in a microfluidic array. The container includes a plurality of walls defining an interior volume and a conductive member for heating the interior volume.

This aspect can have a variety of embodiments. The conductive member can be one of the plurality of walls. The conductive member can be located within the interior volume. The conductive member can be a metal. The conductive member can be in communication with one or more electrically-conductive contacts located on an exterior surface of the container. The container can include a temperature sensor configured to measure a temperature of the microfluidic array. The of the plurality of walls can be optically transparent.

Another aspect of the invention provides container for thermal cycling a plurality of samples in a microfluidic array. The container includes a plurality of walls defining an interior volume and a plurality of conductive members for heating an interior volume.

This aspect can have a variety of embodiments. The plurality of conductive members can be separated by an insulator. The insulator can be air or an adhesive. The plurality of conductive members can constitute one of the plurality of walls. The plurality of conductive members can be located within the interior volume. The plurality of conductive members can be composed of the same material. The plurality of conductive members can be composed of different materials. The plurality of conductive members can have different electrical resistances.

Another aspect of the invention provides a container for thermal cycling a plurality of samples in a microfluidic array. The container includes a plurality of walls defining an interior volume and a first conductive member located in the interior volume and adapted to contact a first end of the microfluidic array.

This aspect can have a variety of embodiments. The first conductive member can be in communication with a first contact located on an exterior surface of the container. The container can include a second conductive member adapted to contact a second end of the microfluidic array. The second conductive member can be located within a mechanical plug configured to substantially seal the container. The second conductive member can be in communication with a second contact located on an exterior surface of the mechanical plug.

Another aspect of the invention provides an apparatus for thermal cycling a plurality of samples in a microfluidic array received in a container. The apparatus includes a first and a second electrical contact and a controller configured to selectively complete the electrical circuit, thereby heating the microfluidic array. The first and the second electrical contacts are configured to form an electrical circuit across the container.

This aspect can have a variety of embodiments. The controller can be a switch. The apparatus can include a power supply in communication with the circuit. The apparatus can include a heat sink. The heat sink can be a fluid bath. The fluid bath can be chilled. The heat sink can be a Peltier element. The apparatus can include a temperature sensor for monitoring the thermal cycling of the microfluidic array. The temperature sensor can be in communication with the controller.

The apparatus can include an imager. The imager can be charge-coupled device. The apparatus can include an illuminator. The illuminator can be one or more light emitting diodes. The illuminator can be a tungsten arc lamp.

The apparatus can include one or more concave mirror configured to illuminate the microfluidic array and an optical fiber bundle configured to channel light from the tungsten arc lamp to the microfluidic array. The apparatus can include a filter wheel configure to condition light before the light is received by the imager.

Another aspect of the invention provides a method for thermal cycling a plurality of samples in a microfluidic array received in a container. The method includes causing electrical current to flow through the container to heat the samples by Joule heating and terminating the flow of electrical current to allow the samples to cool.

This aspect can have a variety of embodiments. The container can include a plurality of walls. The electrical current can flow through at least one of the walls. The electrical current can flow through the microfluidic array within the container. The method can include placing the container in contact with a heat sink. The step of placing the container in contact with a heat sink can include submerging the container in a fluid bath. The step of placing the container in contact with a heat sink can include placing the container against a Peltier element. The method can include imaging the plurality of samples.

Another aspect of the invention provides a method for thermal cycling a plurality of samples in a microfluidic array received in a container. The method includes exposing the microfluidic array to radiation to heat the plurality of samples and terminating the radiation exposure to allow the samples to cool.

This aspect can have a variety of embodiments. The method can include repeating the exposing and terminating steps a plurality of times. The radiation can be microwave radiation or infrared radiation.

Another aspect of the invention provides a through-hole array including: a platen having a first end region a second end region, a plurality of strips spanning from the first end region to the second end region, and a plurality of through-holes located on one or more of the plurality of strips.

This aspect can have a variety of embodiments. The strips can be substantially parallel. The through-hole array can include one or more slots. Each slot can separate two of the plurality of strips. The platen can be formed from a conductive material. The conductive material can be selected from the group consisting of: copper, gold, silver, nickel, iron, titanium, steel, and stainless steel. The plurality of through-holes can be located on one of the plurality of strips are arranged in a single column. The through-holes can have a hydrophilic interior. The through-hole array can include two outer layers of hydrophobic material coupled to a top and a bottom surface of the plurality of the strips. Each of the plurality of through-holes can have a volume less than 100 nanoliters.

Another aspect of the invention provides a container for thermal cycling a plurality of samples in a microfluidic array having a plurality of through-holes arranged on a plurality of strips. The container includes: a plurality of walls defining an interior volume and a plurality of fingers configured to contact the strips when the microfluidic array is inserted in the container.

This aspect can have a variety of embodiments. The container can include a pair of electrically-conductive contacts located on an exterior surface of the container. The contacts can be in communication with the fingers. The fingers can be configured to contact the microfluidic array at a first and a second end of each of the plurality of strips. At least one of the plurality of walls can be optically transparent. The plurality of fingers can be comprised of a metal.

Another aspect of the invention provides a method for thermal cycling a plurality of samples. The method includes providing a through-hole array including a platen having a first end region and a second end region, a plurality of strips spanning from the first end region to the second end region, and a plurality of through-holes located on one or more of the plurality of strips; loading the plurality of samples into the plurality of through-holes; placing the though-hole array in a container; applying a flow of electrical current across the plurality of strips; and terminating the flow of electrical current to allow the samples to cool. The container includes a plurality of fingers configured to contact the strips.

This aspect can have a variety of embodiments. The method can include placing the container in contact with a heat sink. The heat sink can be a fluid bath. The fluid bath can be chilled. The heat sink can be a Peltier element. The method can include imaging the through-hole array.

Another aspect of the invention provides a container for thermal cycling a plurality of samples in a microfluidic array. The container includes: a plurality of walls defining an interior volume, a first port located on a first end of the container, and a second port located on a second end of the container. The first port and the second ports are configured to provide fluid communication with the interior volume.

This aspect can have a variety of embodiments. The second end can be a substantially opposite end of the container with respect to the first end. The first port and the second port can each include a gasket configured to prevent fluid flow when the container is not coupled with a thermal cycler. The container can include a plurality of veins located within the interior volume to promote uniform fluid flow.

Another aspect of the invention provides an apparatus for thermal cycling a plurality of samples in a microfluidic array. The apparatus includes a hot liquid source; a cold liquid source; a pump in fluid communication with the hot liquid source and the cold liquid source; a fluidic circuit coupled to the hot liquid source, the cold liquid source, and the pump; and an interface adapted to couple the fluidic circuit to a container housing the microfluidic array. The container includes a first port and a second port.

This aspect can have a variety of embodiments. The hot liquid source can be a tank. The hot liquid source can be a heater. The cold liquid source can be a tank. The cold liquid source can be a chiller.

The apparatus of claim 1 can include an imager. The imager can be a charge-coupled device. The apparatus can include an illuminator. The illuminator can include one or more light emitting diodes (LEDs). The illuminator can be a tungsten arc lamp. The apparatus can include: one or more concave mirror configured to illuminate the microfluidic array and an optical fiber bundle configured to channel light from the tungsten arc lamp to the microfluidic array. The apparatus can include a filter wheel configure to condition light before the light is received by the imager.

Another aspect of the invention provides a method for thermal cycling a plurality of samples, The method includes: loading the plurality of samples in a microfluidic array; placing the microfluidic array in a container, the container comprising a plurality of walls defining an interior volume, a first port located on a first end of the container, and a second port located on a second end of the container, wherein the first port and the second ports are configured to provide fluid communication with the interior volume; coupling the first port and the second port to a fluidic circuit including a pump, a hot fluid source, and cold fluid source; and alternatively pumping a hot fluid and a cold fluid through the container.

This aspect can have a variety of embodiments. The method can include applying a layer of an immiscible liquid over the microfluidic array. The method can include sealing the container.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein.

DEFINITIONS

The instant invention is most clearly understood with reference to the following definitions:

As used in the specification and claims, the singular form "a", "an" and the include plural references unless the context clearly dictates otherwise.

The term "biocompatible" denotes a natural or artificial substrate that supports cellular adhesion or proliferation without eliciting a toxic or other undesirable effect in a cell in contact with the substrate.

DETAILED DESCRIPTION OF SPECIFIC EMBODIMENTS

New apparatus and methods for thermal cycling specimens are provided herein. The methods are applicable to specimens held in a variety of laboratory vessels and are particularly advantageous when used in conjunction with specimens held in a through-hole array.

Through-Hole Arrays

Through-hole arrays generally consist of a platen having a plurality of through-holes extending from a first surface of the platen to a second surface of the platen. The platen can be fabricated from a variety of materials including metals (e.g. copper, gold, silver, nickel, iron, titanium, and alloys thereof such as steels and stainless steels), plastics, conductive silicon, glass, other rigid materials, semi-rigid materials, flexible materials, and the like.

Figure 1:
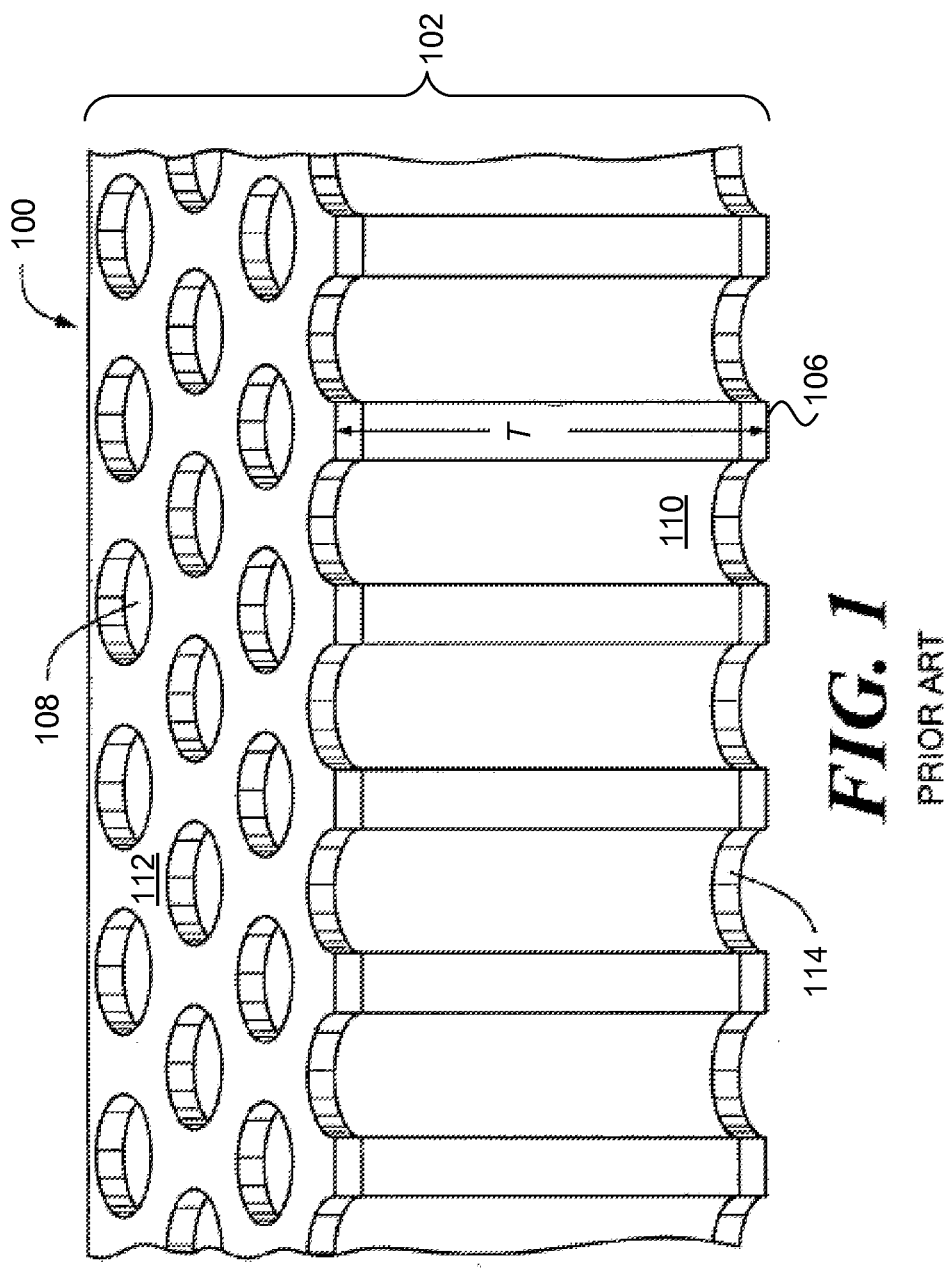
FIG. 1 depicts an exemplary embodiment of a through-hole array for use with various embodiments of the invention.

FIG. 1 shows a cutaway view of a exemplary microfluidic through-hole array of through-holes. The sample array 100 includes a thin plate of material 102 having a pair of opposed surfaces 104, 106 and a thickness. A large number of through-holes 108 (e.g. 384 or 3,072 through-holes) penetrate through the thickness from one of the surfaces 104 to the other opposing surface 106 (not shown). Through-holes 108 can, in some embodiments, be arranged in groups (e.g. 12×4 groups of 8×8 through-holes 108) for ease of loading, reference, and interfacing with standard 96- or 384-well microtiter plates.

The sample array 100 can, in some embodiments, have a thickness T from 0.1 mm to more than 10 mm, for example, around 0.3 to 1.52 mm or 0.5 mm. Typical volumes of the through-holes 12 can range from 0.1 picoliter to 1 microliter, with common volumes in the range of 0.2-100 nanoliters, for example, about 35 nanoliters. Capillary action or surface tension of the liquid samples can be used to load the sample through-holes 108. For typical plate dimensions, capillary forces exceed gravitational and inertial forces on the liquid retained in each hole. Plates loaded with sample solutions can readily handled and even centrifuged at moderate speeds without displacing samples.

The use of through-holes 108, as compared to closed-end well structures, reduces the problem of trapped air inherent in other microplate structures. The use of through-holes together with hydrophobic and hydrophilic patterning enables self-metered loading of the sample through-holes 108. The self-loading functionality helps in the manufacture of arrays with pre-loaded reagents, and also in that the arrays will fill themselves when contacted with an aqueous sample material.

Suitable through-hole arrays are available under the OPENARRAY® trademark from BioTrove, Inc. of Woburn, Mass. and are described in U.S. Pat. Nos. 6,306,578; 6,387,331; 6,436,632; 6,716,629; 6,743,633; 6,893,877; 7,332,271; and U.S. Patent Application Publication Nos. 2001/0055765; 2002/0151040; 2002/0192716; 2003/0124716; 2003/0180804; 2004/0037748; 2004/0171166; 2004/0191924; 2004/0208792; 2005/0059074; 2005/0079105; 2005/0148066; 2005/0230213; 2006/0105453; 2006/0183171; 2007/0003448; and 2008/0108112.

Coated Through-Hole Arrays

To enhance the capillary action of the through-holes 108, the target area of the receptacle, interior walls 110, can have a hydrophilic surface that attracts a liquid sample. It is often desirable that the surfaces be biocompatible and not irreversibly bind biomolecules such as proteins and nucleic acids, although binding may be useful for some processes such as purification and/or archiving of samples. Alternatively, the sample through-holes 108 can contain a porous hydrophilic material that attracts a liquid sample. To prevent cross-contamination (crosstalk) between the through-holes, the exterior planar surfaces 112 of plate 100 and a layer of material 114 around the openings of sample through-holes 108 can be hydrophobic or can be coated with a hydrophobic material. In one embodiment, the interior walls 110 are made hydrophilic by covalently linking polyethylene glycol (PEG) or other similar hydrophilic and biocompatible molecules to the surface and the exterior 114 is made hydrophobic by covalent bonding of fluoroalkylsilane or similar hydrophobic molecules to the surface. Thus, each through-hole 108 can have an interior hydrophilic, biocompatible region 110 bounded at either end by a hydrophobic region 114.

Exemplary methods for coating through-hole arrays are briefly described below and are described in greater detail in U.S. Patent Application Publication No. 2006/0105453.

In one embodiment, one or more plates are first cleaned in a solution of about 10% RBS®-35 detergent, available from Thermo Fisher Scientific Inc of Rockford, Ill., at about 50° C. for about two hours. C8 vinylsilane (7-octenyltrimethoxysilane) is then applied through vapor deposition for about 2.5 hours at about 150° C. to form a reactive vinyl monolayer.

In order to introduce an oxidizing solution into the through-holes to remove the hydrophobic vinyl monolayer, a "forced loading" technique can be used. The plates are first dipped in a lower energy (surface tension) liquid such as ethanol, which is retained in the through-holes. The plates are then immersed in water, which replaces the ethanol in the through-holes. The plates are then placed in a loading chamber containing an oxidizing solution containing about 360 mL of about 5 mM $KMnO_4$ and about 40 mL of about 19.5 mM $NaIO_4$ floating on an immiscible fluid such as FLUORINERT® FC-3283. The fluid level is raised to fill the through-holes with the $KMnO_4/NaIO_4$ solution. The plates are then incubated for about two hours. The plates are then placed in a chamber containing a solution containing 400 ml of 15 mg/mL EDC (1-ethyl-3-(3-dimethylaminopropyl) carbodimide hydrochloride) and 5 mg/mL polyethylene glycol (PEG) floating on an immiscible fluid such as FLUORINERT® FC-3283. The solution level is again raised to fill the through-holes with the solution and the plates are again incubated for about two hours in the solution. The plates are then dried overnight at about 100° C. under vacuum with any EDC and PEG present in the solution.

The plates are then reloaded with a solution containing about 50 mg/mL of a high-weight PEG (e.g. PEG 8000) floating on an immiscible fluid such as FLUORINERT® FC-3283 so that the through-holes are filled with the solution. The fluid level is lowered to remove the PEG solution from the through-holes before removing the plates from the chamber. The plates are then dried for about three hours at about 100° C. under vacuum.

A hydrophobic coating is re-applied by placing the plates in a vapor deposition chamber for about two hours at about 150° C. and exposed to perfluorotriethoxysilane and/or vinylsilane. The plates are then cured in gaseous ammonia for about 30 minutes. The resulting hydrophobic surfaces can be characterized by contact angles about 90°, for example greater than about 100°, about 110°, about 120°, about 130°, about 140°, about 150°, about 160°, about 170°, or about 180°. The plates are then rinsed to remove excess physisorbed PEG from the through-holes along with the perfluorosilane film deposited on the top excess PEG.

In some embodiments, the plates are cleaned in an RBS®-35 solution as described and placed in a microwave-generated plasma with a trace amount of water to remove any organic debris on the plate surface and to functionalize the surface with hydroxyl groups. The plates are then further processed as described.

Exemplary Uses of Through-Hole Arrays

In various embodiments, through-hole arrays can be used as follows. Reagents for implementing different biochemical or biological analyses of one or more biological samples are loaded into the through-holes. For example, in the case of PCR analyses, each through-hole can contain a different primer pair or different primer-probe set. Biological samples mixed with PCR reagents (e.g. MASTERMIX® reagents available from Applied Biosystems of Foster City, Calif.) are then loaded into one or more through-holes.

The through-hole array is then inserted into a case containing an immiscible, optically transparent liquid that acts as an evaporation barrier. Suitable immiscible liquids include FLUORINERT® coolants (e.g. FLUORINERT® FC-77, having a chemical formula of $C_8F_{18}$), silicon oil, or mineral oil. FLUORINERT® coolants are available from the Minnesota Mining and Manufacturing Company of St. Paul, Minn. Other desirable physicochemical properties of the immiscible liquid are a moderate thermal conductivity and a low electrical conductivity.

Through-Hole Array Cases

Figure 2A:
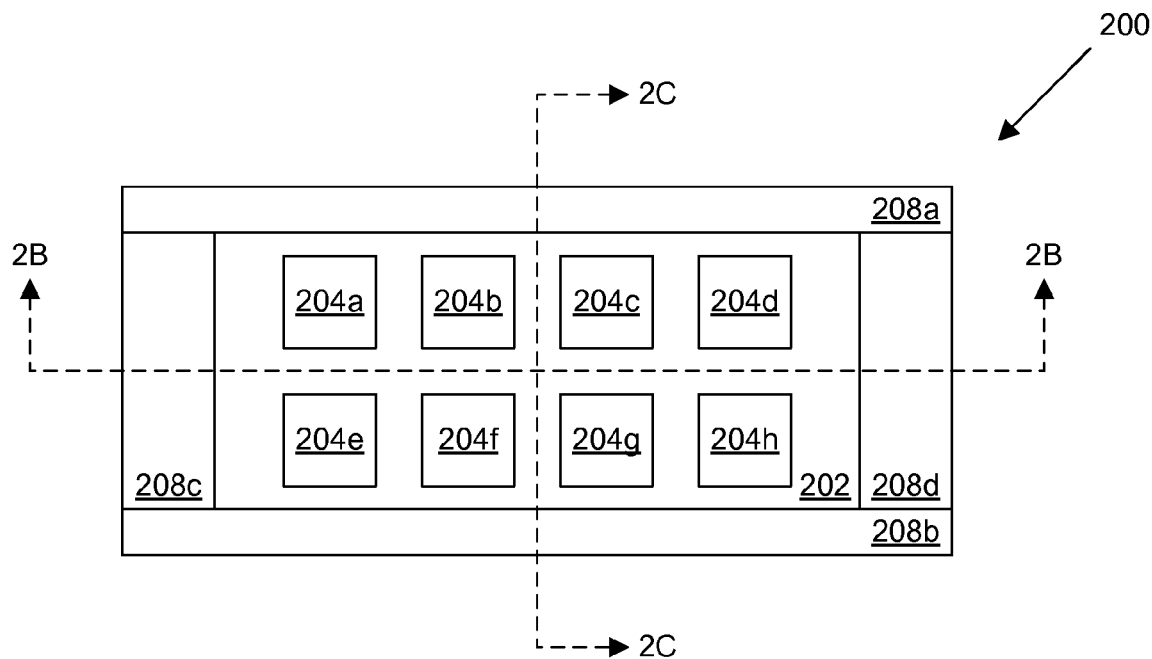
FIGS. 2A-2C depict a case for holding a through-hole array according to one embodiment of the invention.
Figure 2B:
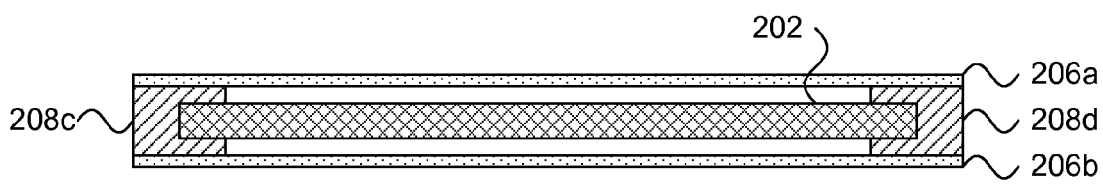
Figure 2C:
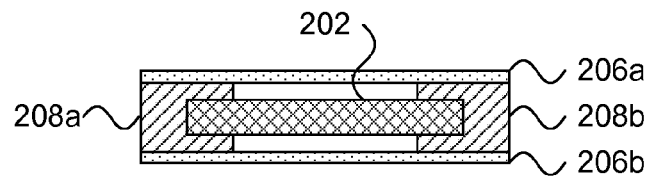

FIGS. 2A, 2B, and 2C depict a case 200 for holding a through-hole array according to one embodiment of the invention. FIG. 2A provides a top view of the case 200, while FIGS. 2B and 2C provide cross-sectional views of the case 200. Case 200 is designed to hold a through hole array 202, which can contain a plurality of groups 204a-204h of through-holes (not depicted).

Case 200 can be formed from a variety of materials capable of holding through-hole array 202 and immiscible liquid (not depicted). In one embodiment, the case 200 is fabricated from two platens 206a, 206b connected by one or more gaskets 208a-208d. The platens can include a variety of materials such as glass, plastics, metals, and the like. In some embodiments, at least one of platens 206a, 206b are optically transparent to allow for monitoring of reactions in the through-hole array during thermal cycling or during isothermal amplification reactions. Additionally or alternatively, one of the platens 206a, 206b can be optically opaque and/or non-reflective to minimize unwanted reflections when imaging.

In various embodiments where the rapid heating and/or cooling of the through-hole array 202 is desired, thinner platens 206a, 206b can be used. Thermal conduction through glass scales in proportion to thickness. Accordingly, the use of microscope slide covers, which are about 170 micrometers thick, facilitates rapid heat transfer. Cooling rates of at least 10° C./second can be achieved utilizing a case constructed in this manner and the systems and methods described herein.

In another embodiment, one or more of the platens 206a, 206b can be composed of a material with a high thermal conductivity. For example, one or more of the platens 206a, 206b can be composed of metals such as gold, silver, copper, iron, brass, aluminum, and allows thereof. To further increase conduction, one or more of the platens 206a, 206b can include one or more vanes or protuberances to increase the surface area in contact with a heat sink.

The gaskets 208a-208d can be formed from a variety of materials such as plastics, rubbers, resins, metals, and the like. In one embodiment, one or more of the gaskets 208a-208d are a liquid crystal polymer (LCP), for example, a liquid crystal polymer containing 40% glass fiber. Suitable LCPs are available under product number RTP 3407-3 from RTP Company of Winona, Minn. The gaskets 208a-208d and platens 206a, 206b can be bonded with a variety of adhesives selected for the particular materials of the gaskets 208a-208d and platens 206a-206b. In some embodiments, gaskets 208a-208d and platens 206a, 206b are be bonded with transfer adhesive tape (e.g. 3M® Adhesive Transfer Tape 468 MP, available from the Minnesota Mining and Manufacturing Company of St. Paul, Minn. In some embodiments, the gaskets 208a-208d and platens 206a, 206b are plasma irradiated within 24 hours prior to assembly to improve bonding strength.

Although depicted as four distinct gasket components 208a-208d, one or more gasket components 208a-208d can be combined into a single gasket component. For example, gasket components 208a, 208b, 208c can be a single U-shaped gasket, while gasket component 208d is inserted after the through-hole array 202 is inserted into the case 200. One or more gasket components can be composed entirely from an adhesive (e.g. a UV-curable adhesive such as DYMAX® OP-29V, available from DYMAX Corporation of Torrington, Conn.) applied after the through-hole array 202 is inserted into the case 200. In another embodiment, gasket components 208a-208d form a single gasket and platen 206a or 206b is bonded to the gasket after the through-hole array 202 is inserted.

As depicted in FIGS. 2A-2C gasket components 208a-208d can optionally have a U-shaped groove to hold the through-hole array 202 away from platens 206a, 206b. A variety of other suitable case designs and features are described in U.S. Patent Application Publication Nos. 2004/0208792 and 2006/0094108.

In one embodiment of the invention, Joule heating is used to heat the samples held in through-hole array 202 during the thermal cycling process or to hold the plate at a constant temperature for isothermal amplification. To facilitate electrical flow through the through-hole array 202 while protecting the samples held therein from evaporation by case 200, one or more gasket components (e.g. 208a and 208b, or 208c and 208d) can include electrically conductive materials. In some embodiments, the gasket components 208a-208d include distinct conductive portions (e.g. wires extending from an interior portion of the gasket component 208a-208d in contact with the through-hole array 202 to an exterior portion of the gasket in contact with an electrical source). In other embodiments, the gasket is composed of an electrically conductive material such as conductive resin (e.g. a resin impregnated with a conductive material such as copper, gold, silver, nickel, stainless steel, nickel-coated graphite, carbon black, carbon powder, carbon fibers, and the like). Conductive resins are available from RTP Company of Winona, Minn. and Cool Polymers of Warwick, R.I. In another embodiment, Joule heating of the platen is accomplished by induction heating by radio or microwave frequency radiation.

One or more gasket components 208a-208d can be hermetically sealed to platens 206a, 206b so that no liquid leaks from the case. However, not all gasket components 208a-208d need to form a leak-tight, hermetic seal. For example relaxing the requirement that "top" component of the gasket (e.g. 208d) be leak-tight during temperature cycling simplifies the case design, manufacture and use.

Thermal Cyclers

Figure 3:
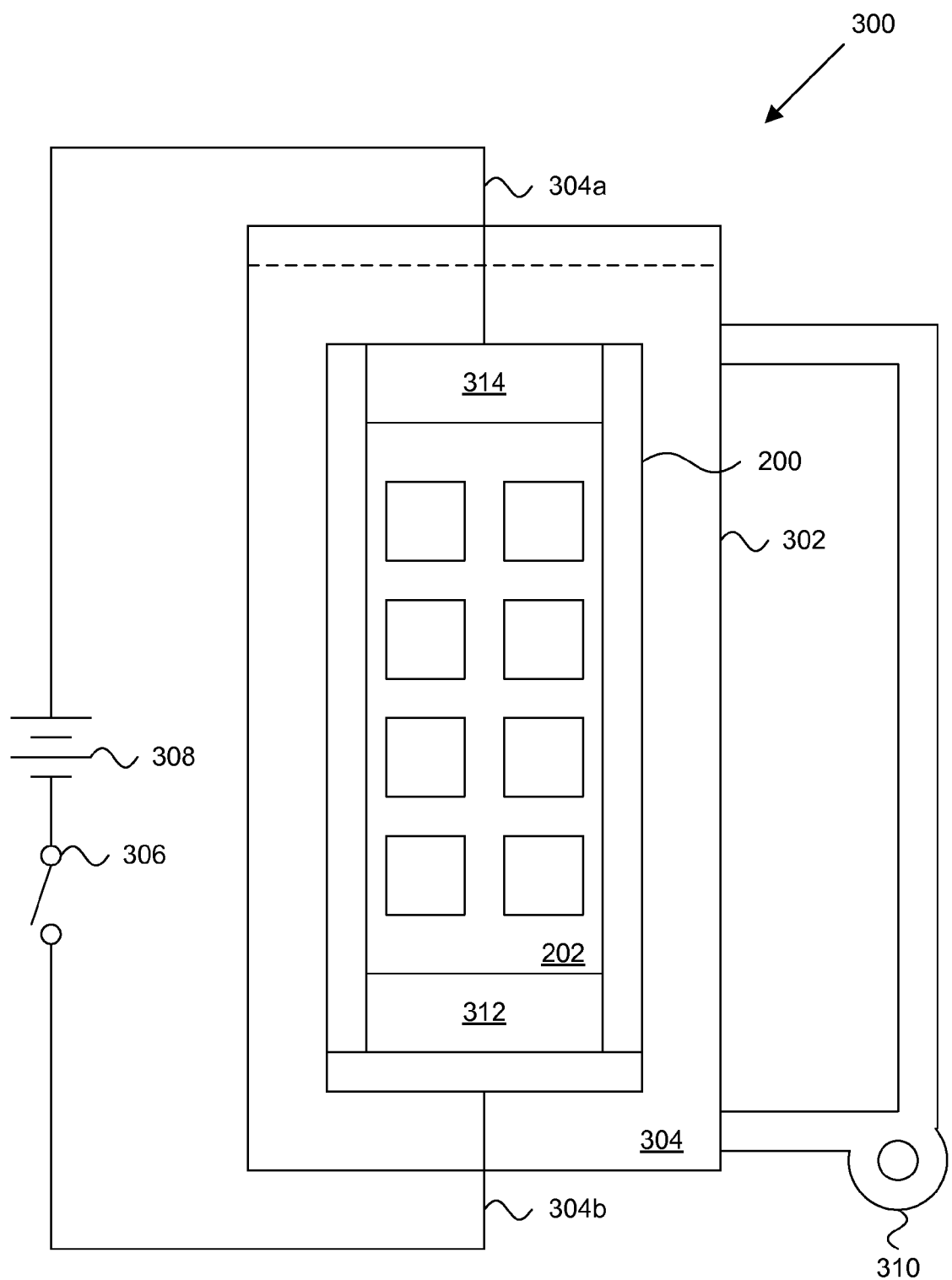
FIG. 3 depicts a thermal cycler for the rapid thermal cycling of samples held in a through-hole array within a case according to one embodiment of the invention.

Referring to FIG. 3, a thermal cycler is provided for the rapid thermal cycling of samples held in a through-hole array 202 within a case 204. The case 200 is connected to electric leads 304a, 304b. When switch 306 is closed, electricity flows from power source 308 through case 204 and/or through-hole array 202. The electrical resistance of case 204 and/or through-hole array 202 generates heat, which is conductively transferred to the samples contained therein.

The through-hole array 202 can be cooled during the annealing phase by a variety of means. For example, the case 204 can be in contact with the atmosphere. In order to speed cooling, an active cooling means such as a fan can be employed. In the illustrated embodiment of FIG. 3, the case 200 is placed within a vessel 302 containing liquid 304. The liquid 304 is ideally an optically transparent liquid with a high heat capacity such as water or refrigerant such as FLUORINERT® coolant (e.g. FLUORINERT® FC-70 or FC-77) or a water/ethanol mixture.

Vessel 302 can be a closed vessel or can be open to the atmosphere. Vessel 302 can be wholly or partially formed from a optically transparent material such as glass. In some embodiments, portions of the vessel 302 can be optically opaque and/or non-reflective to reduce ambient reflections that could interfere with imaging of the samples.

The refrigeration liquid 304 is cooled to a low and substantially constant temperature by a refrigerator unit 310 to a temperature above the liquid freezing point, making the temperature difference between the platen 202 and liquid heat sink 304 large. This, in turn, facilitates rapid heat flow from the heated platen 202 into the cooled liquid 304.

The temperature of the through-hole array 202 can, in some embodiments, be monitored to verify that the samples are sufficiently heated. For example, a temperature sensor, such a thermometer, a bi-metal mechanical thermometer, a thermocouple, a liquid crystal thermometer, and the like can contact the through-hole array, the case, and/or the liquid 304. Alternatively, an infrared thermometer can measure the temperature of the through-hole array and/or the samples. In another embodiment, a thermistor can be used to measure the temperature based on changes in the resistance of the through-hole array 202 and/or case 204 as the temperature changes.

One method for heating and cooling the array to implement the polymerase chain reaction (PCR) is described below. PCR is described in greater detail in a variety of publications such as Shadi Mahjoob, *Rapid microfluidic thermal cycler for polymerase chain reaction nucleic acid amplification*, 51 Int'l J. of Heat and Mass Transfer 2109-22 (2008).

Starting at a basal temperature, switch 306 is closed and an electrical current (e.g. about 100 Amps (A), about 200 A, about 300 A, about 400 A, about 500 A, about 600 A, and the like) is injected into the through-hole array 202, heating the array 202 and the liquid retained in the through-holes. After the through-hole array reaches the desired temperature (e.g. 98.26° C.—the melting temperature for double-stranded DNA), the switch opens to break the current flow. In some embodiments of the invention, heat conduction from the array rapidly drops the liquid temperature to a lower value (e.g. 55° C.—the annealing temperature for DNA). When the array temperature has dropped to a prescribed level, the switch 306 is closed, current is re-injected into the array 202 and resistive heating increases the array temperature to a higher set-point level (e.g. 98.26° C.—the melting temperature for double-stranded DNA). Various embodiments of the invention can heat the array to a melting temperature for double-stranded DNA in less than one second (e.g. about 200 ms, about 250 ms, about 300 ms, about 350 ms, about 400 ms, about 450 ms, about 500 ms, about 550 ms, about 600 ms, about 650 ms, about 700 ms, about 750 ms, about 800 ms, about 850 ms, about 900 ms, about 950 ms, and the like). This process can be automated and performed cyclically to increase/decrease temperature of the array as required for implementation of the PCR assay or to hold the array at a constant temperature, above or below ambient temperature, as prescribed for isothermal reactions or cell culture.

Temperature differences resulting from non-uniform current injection and thermal conductivities of the through-hole array 202 and/or the case 200 can be compensated for by injecting current at different points on the through-hole array 202 and/or the case 200. For example, instead of injecting current at one end and exiting the opposing end, lengthwise along the through-hole array 202 and/or the case 200, current can be injected along the long side of the through-hole array 202 and/or the case 200 and exit from the opposing edge.

Figures 4A, 4B:
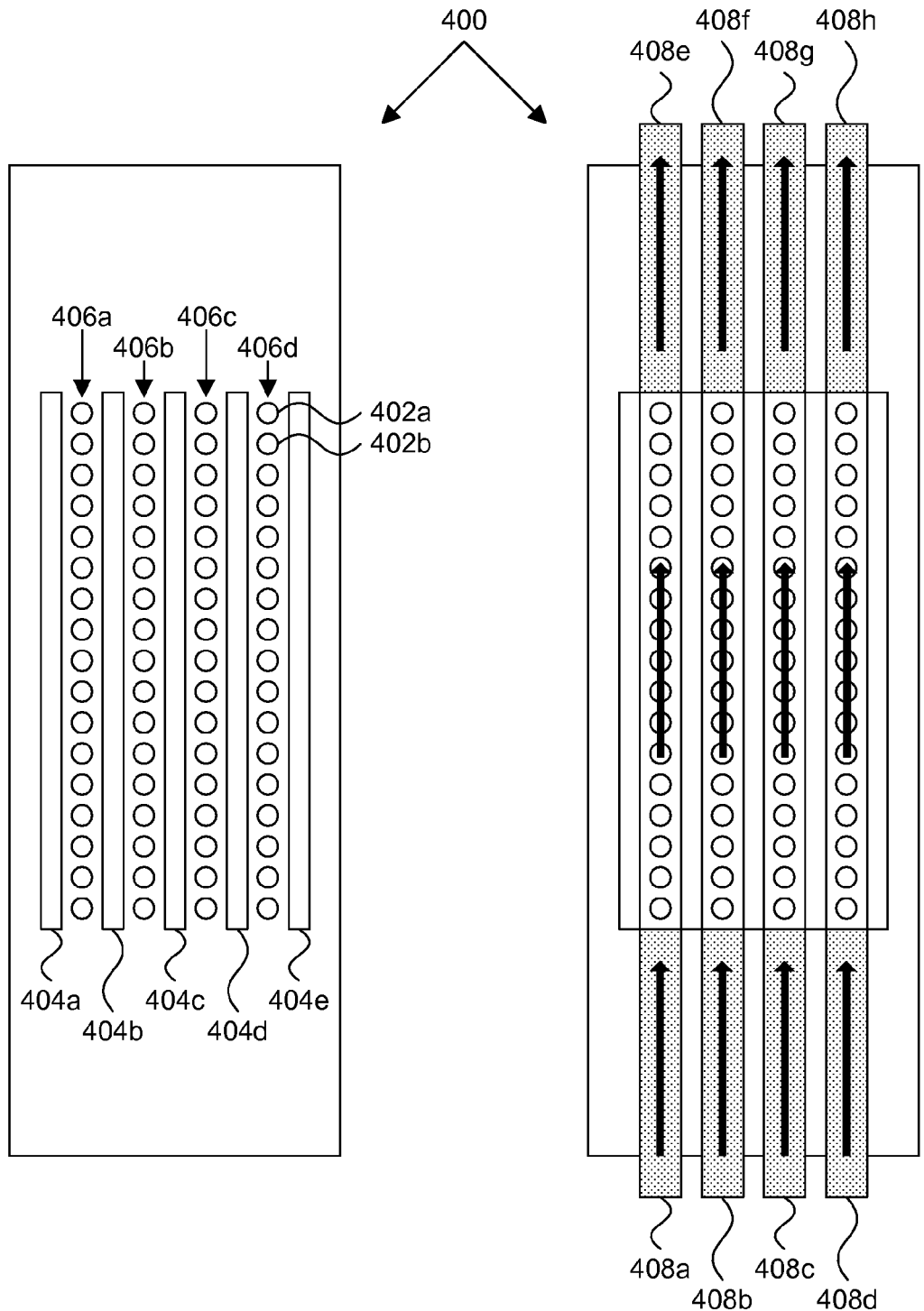
FIG. 4A depicts an embodiment of a through-hole array in which through-holes are arranged on strips according to one embodiment of the invention.
FIG. 4B depicts the application of a plurality of conductive fingers to contact the end of strips on the through-hole array to direct electrical current through the strips according to one embodiment of the invention.

Alternatively, the through-hole spatial distribution, size, geometry and spacing can be modified to achieve uniform heating. FIG. 4A depicts one exemplary embodiment of such a through-hole array 400. A plurality of through-holes 402a, 402b and slots 404a-404e are formed such that the through-holes 402a, 402b are arranged on strips 406a-406d. As depicted in FIG. 4B, to heat the through-hole array, a plurality of conductive fingers 408a-408h contact the end of strips 406a-406d to direct most of the electrical current (represented by arrows) through strips 406a-406d.

Isothermal Amplification

In another embodiment of the invention, the temperature of the plate is held at a substantially constant temperature (e.g. about 42° C. for the Transcription Mediated Amplification (TMA) assay) by a series of current pulses modulated by feedback from a thermal sensing element (e.g. a thermal sensing element in contact with the platen).

Through-Hole Array Imaging System

FIG. 5A depicts an embodiment of a system 500a that provides optical access to a through-hole array 202 while the through-hole array 202 is heated and cooled. System 500 can implement protocols such as the real-time PCR process for quantitative measurement of gene expression, isothermal amplification for quantitative measurement of gene expression, and/or recordation of activities of cells loaded into each channel of the array.

In system 500, a pair of light emitting diodes (LEDs) 502a, 502b obliquely illuminate the array 202 in a transillumination configuration and the light either passed through the array channels 504 or emitted from each through-hole 504 of the array (e.g. fluorescence) is recorded by an electronic camera 506. A filter wheel 508 containing neutral density or spectrally selective filters is optionally included to intensify or spectrally condition the light before it is recorded by the camera 506 (e.g. a charge-coupled device, referred to herein as a "CCD").

The LED light sources 502a, 502b are controlled by an electronic controller 510 via wires 512a, 512b and synchronized to the temperature modulation of the through-hole array 202 to effect a given application. Electronic controller 510 can also control camera 506 via wires 514 and/or filter wheel 508 via wires 516. Electronic controller 510 can also control the heating of array 204 by supplying electric current via wires 518a, 518b.

The LEDs 502a, 502b can be turned on or off (e.g. strobed) or intensity modulated and gated relative to the image capture/recording by the electronic camera 506. The oblique illumination described in this embodiment is advantageous because it minimizes direct illumination of the camera 506 by light from the LEDs 502a, 502b and only the scattered or emitted light from the array through-holes 504 is received by the camera 506, resulting in a high contrast image because of the lower background light.

Alternatively, the through-hole array 202 is illuminated through a through a dichroic filter and the fluorescence emission from the through-hole array 202 is reflected from the filter and directed towards an optical detection element.

Images of the through-hole array 202 are captured by the camera 506 and processed to extract information on biological or chemical activity in each through-hole 504 of the through-hole array 202. For example, fluorescent images of the PCR reaction at the primer annealing temperature taken at each temperature cycle can be processed with well-known image processing algorithms for quantitative assessment of transcript copy number in each channel of the array. Such algorithms are described in publications such as U.S. Pat. Nos. 6,814,934; 7,188,030; 7,228,237; and 7,272,506.

Figure 5:
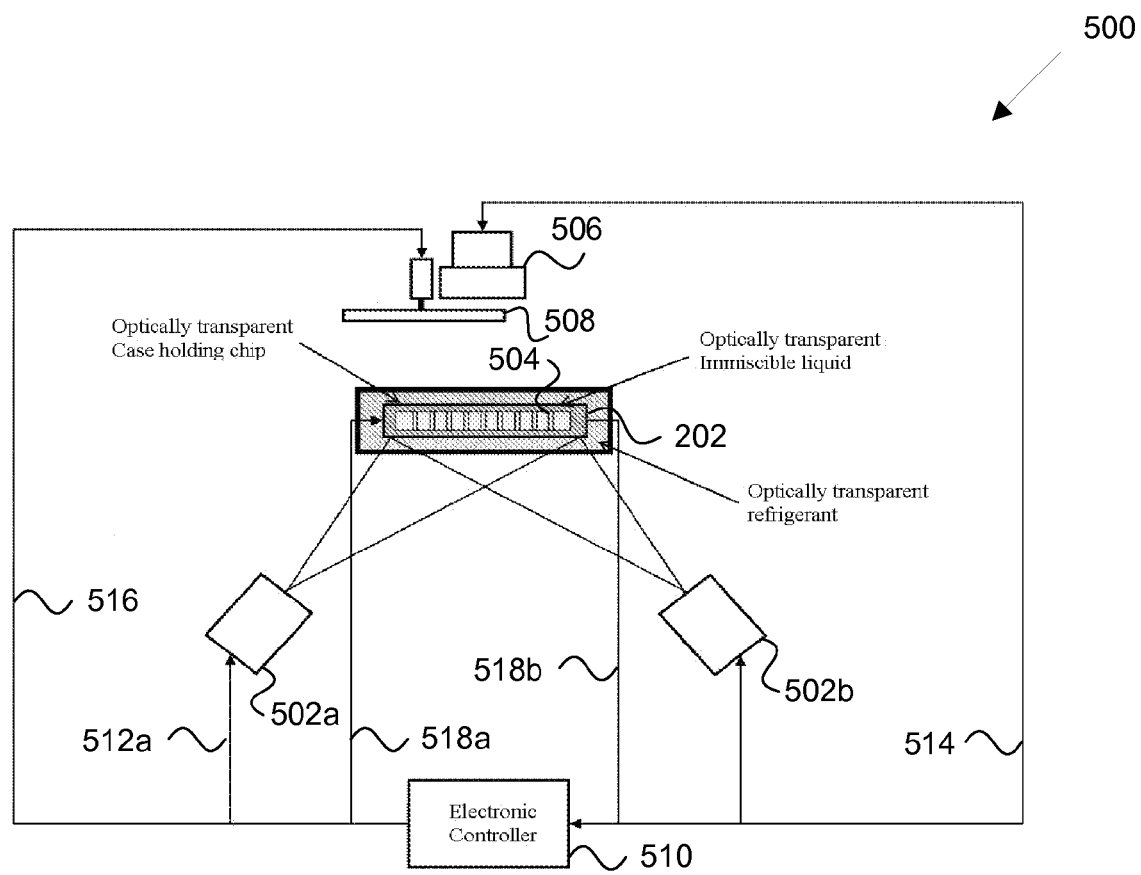
FIG. 5 depicts a system that provides optical access to a through-hole array while the array is heated and cooled according to one embodiment of the invention.
Figure 6:
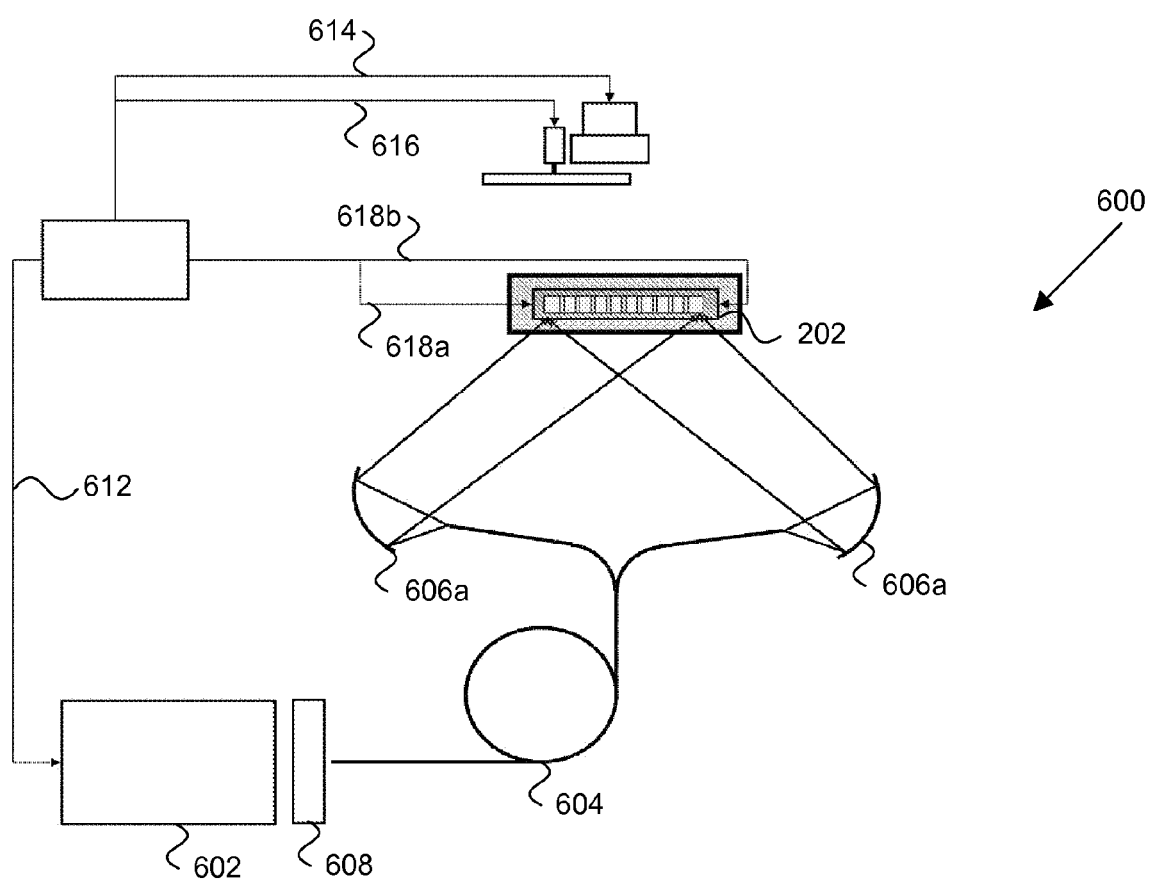
FIG. 6 depicts a system that provides optical access to a through-hole array from a single light source while the array is heated and cooled according to one embodiment of the invention.

Alternatively, epi-illumination schemes well-known in the art could be implemented to achieve a performance similar to the transillumination scheme thus described. An exemplary embodiment is described in FIG. 6 wherein the dual LED light source 502a, 502b of FIG. 5 is replaced by a single light source 602 illuminating a through-hole array 202 through an optical fiber bundle 604 and a pair of concave mirrors 606a, 606b for oblique illumination of through-hole array 202. One example of the light source 602 is a tungsten arc lamp collimated and conditioned by neutral density or spectrally selective filters 608 prior to illumination of the through-hole array 202. As in FIG. 5, electronic controller 610 can control light source 602, camer 606, and filter wheel 608, as well as the heating of array 202 via wires 612, 614, 616, 618a, and 618b.

In another embodiment, the dual LED light source 502a, 502b of FIG. 5 is replaced by a multi-element LED array. The LED wavelength is chosen to excite the fluorescent probe in the samples (such as the SYBR® Green dye, available commercially from sources such as Applied Biosystems of Foster City, Calif. and Qiagen Inc. of Valencia, Calif.) and the LED element spacing is chosen to match the groupings of through holes. For example, in one embodiment of the through-hole array, subarrays of 8×8 through-holes are set on a 4.5 mm apart such that the total 3,072 hole array is comprised of 4×12 subarrays. In this embodiment an 8×12 array of LEDs would illuminate the through-hole array.

Figure 7A:
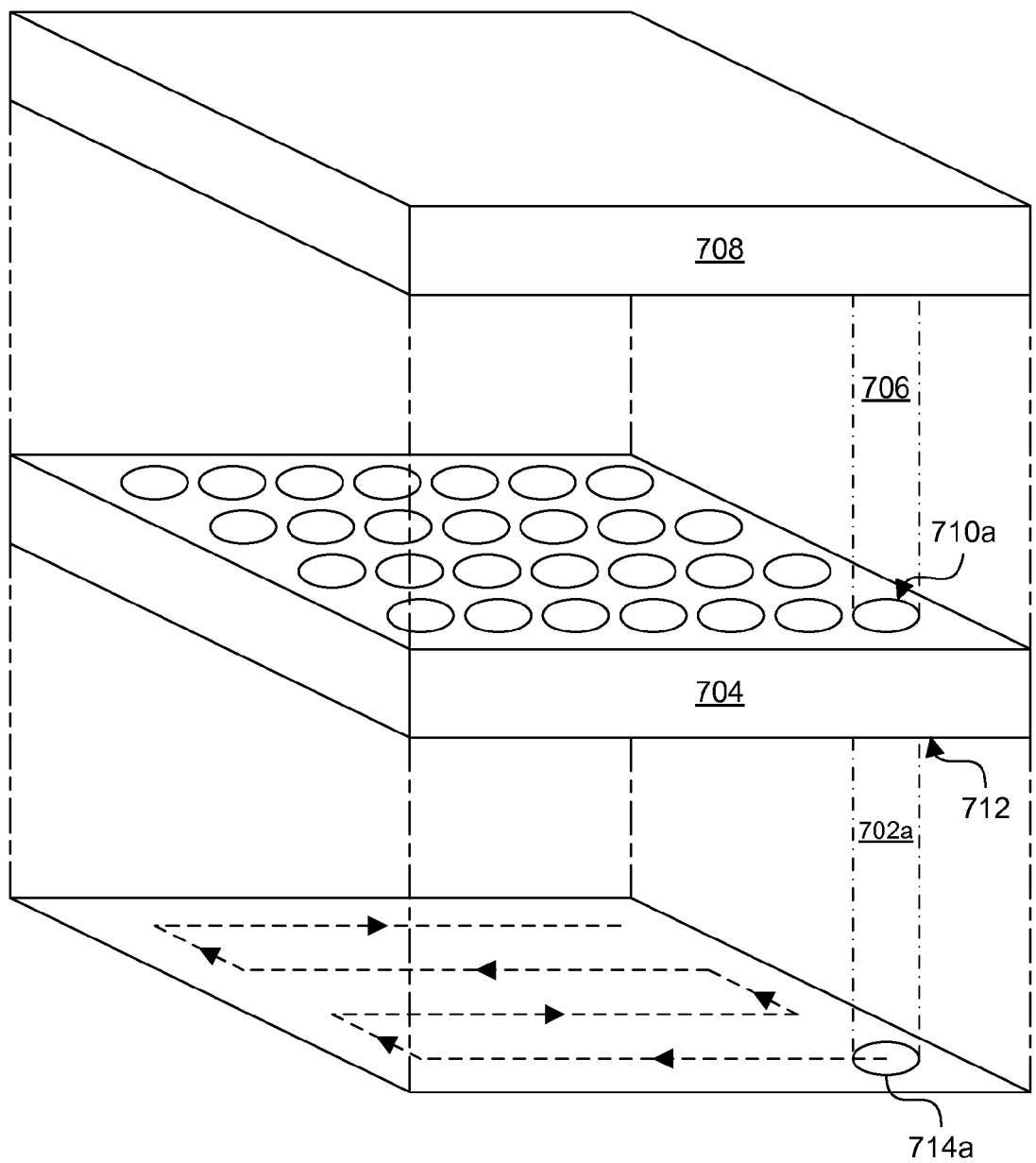
FIGS. 7A and 7B depict fast scanning systems according various embodiments of the invention.

In yet another embodiment, the CCD-based imaging system is replaced with a fast scanning system. In one example of a fast scanning system depicted in FIG. 7A, a focused light beam 702 is scanned in two dimensions across a through-hole array 704 and the fluorescence emission 706 from the array 704 is directed towards an optical detector 708a. Fluorescence 706 from each through-hole 710a is related to the light beam position on the array surface 712. In one embodiment, light source 714 can move relative to the array 704 such that light beam 702 is substantially perpendicular with array surface 712. Alternatively, light source 714 can be stationary while the angle of the light 712 is modulated to focus on particular through-holes 710.

Figure 7B:
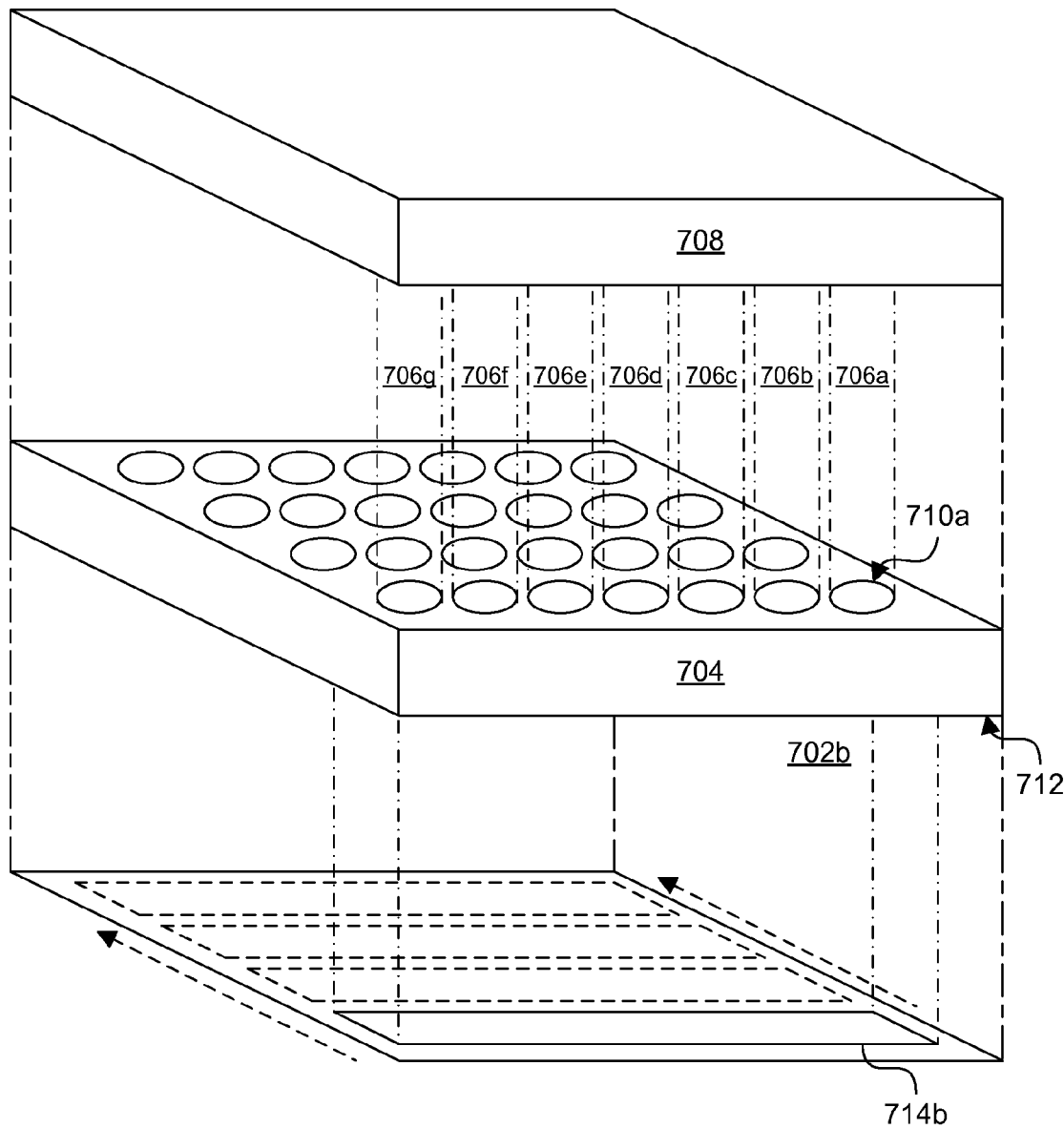

An alternative approach depicted in FIG. 7B involves scanning a line-focused light beam 702b in one dimension across the array 704 and directing fluorescence emissions 706a-706g towards a two-dimensional optical dector 708b such as a CCD camera. Fluorescence from each through-hole 710 is determined by instantaneous position of the focused light beam 702 on the platen surface 712.

High-Speed Through-Hole Array Cases

Another embodiment of a thermal control device 800 is depicted in FIGS. 8A and 8B. The top and bottom surfaces (804 and 806, respectively) of a case 802 enclosing a through-hole array 202 are fabricated from thin rigid plates separated by a polymer spacer with a lengthwise slot for holding the through-hole array 202 along its edge to maintain a thin uniform gap between the top and bottom plates defining the case 802. In some embodiments, at least one of the plates 804, 806 is lapped or ground flat so as to provide intimate thermal contact with the flat block 810 of a thermal cycler. Additionally or alternatively, a flexible, thermally conductive polymer 812 can be attached to the plate to provide the requisite intimate thermal contact with the thermal cycler block. In some embodiments, the top plate 804 is that it is optically transparent for illumination of the through-hole and detection of the resulting fluorescence emission from each microchannel of the array 202.

A thin adhesive layer mechanically connects the two plates 804, 806 to the spacing 808, forming a hermetic seal. To prepare the cassette for thermal cycling, the case is partially filled with an immiscible liquid (e.g. FLUORINERT® coolant), a through-hole array 802 loaded with PCR reagents and nucleic acid sample is inserted into the case 802, and the case is hermetically sealed with a plug of UV curable epoxy 814 such as DYMAX® OP-29V. The assembled case or cassette is placed onto a flat block thermal cycler 810 and thermally cycled according to a prescribed protocol suitable for implementing the PCR method.

One difference between the presently discussed embodiment and previous cases is the use of a high thermal conductivity, low specific heat material such as a metal, ceramic or diamond for platen instead of a low thermal conductivity, high specific heat material such as glass. The rapid conduction of heat through the platen will decrease the thermal cycle time accordingly. If the both sides of the array package require optical transparency, then a material such as diamond is a reasonable choice. A second option is to reduce the thickness of the platen plates to minimize the temperature difference across the plate and therefore the thermal transfer impedance.

Through-hole Array Temperature Modulation by Electrically Conductive Cases

Figure 8:
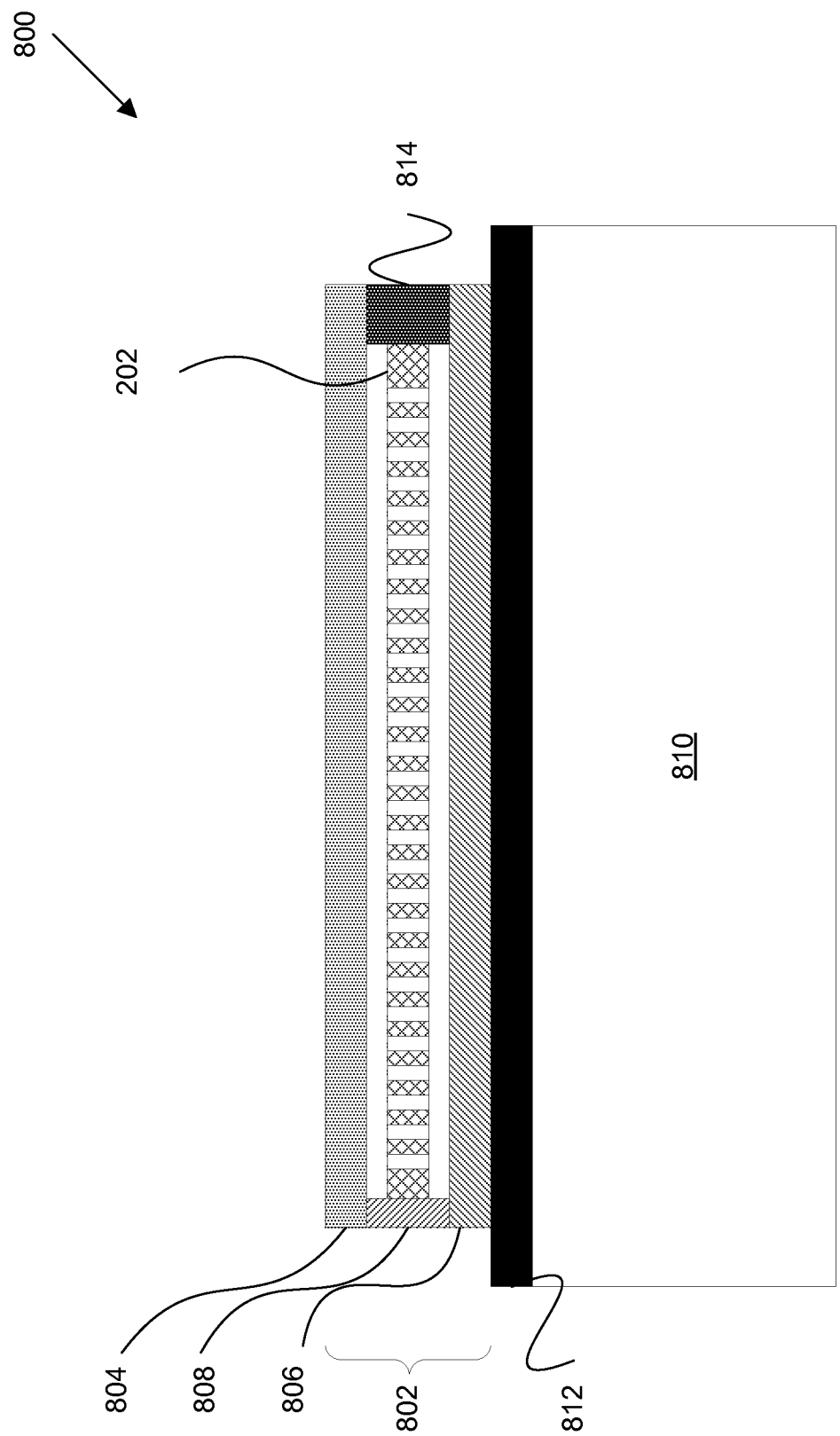
FIGS. 8 and 9 depict thermal control devices according to various embodiments of the invention.
Figure 9:
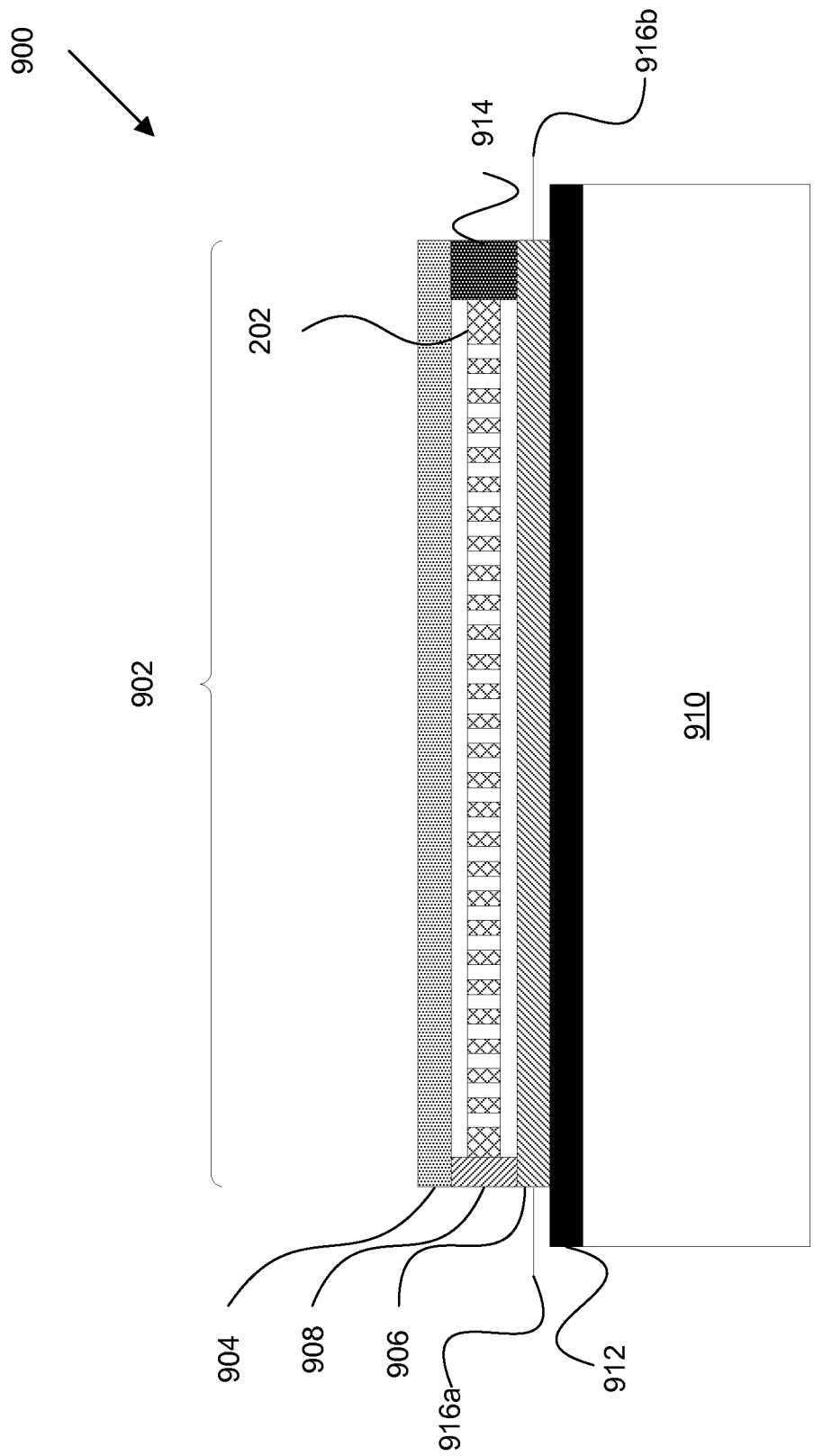

Another embodiment, depicted in FIG. 9, modifies the system 800 of FIG. 8 to replace the flat block thermal cycler 810 with a constant-temperature heat sink 910. The case 902 is fabricated with a bottom platen 906 that is thermally and electrically conductive and placed in intimate thermal contact with a constant temperature heat sink 910 kept at a temperature substantially below the PCR annealing temperature. For example, the heat sink 910 can be cooled to between about −20° C. to about 30° C., which is below the PCR annealing temperature range of about 35° C. to about 65° C. and above typical coolant pour temperatures of about −25° C. The bottom platen 906 is electrically isolated from the heat sink 910 by a thin thermally conductive, electrically insulating dielectric layer 912. Suitable dielectrics include glass, ceramics, and diamond.

The platen is electrically connected to an external current source and a electronically controlled switch (not depicted) by electrical contacts (e.g. wires 916a, 916b). Closing the switch causes electrical current to pass through the platen, causing the platen to heat from ohmic loss in the metal. The thermal power P produced by this method is P=i² R, where i is the instantaneous current through the metal and R is the plate's bulk resistance.

Heat from the platen 906 flows partially into the heat sink 910 and partially into the through-hole array 202 by way of the intervening fluid. Opening the switch stops the flow of current and production of heat within the platen 910. Heat now flows out of the through-hole array 202 and into the lower temperature heat sink 910. The rate of heat transfer into and out of the case 902 is governed by the thermal conductivity and specific heat of the materials between the array 202 and the heat sink 910, as well as the thermal properties of the array 202 and the heat sink 910 themselves.

To reach and maintain a specified array temperature, at least one thermal sensor in intimate thermal contact with the though-hole array 202 can provide a temperature signal for controlling the duration and frequency of the switch opening and closing, thereby modulating the electrical current through the platen 906.

Figure 10B:
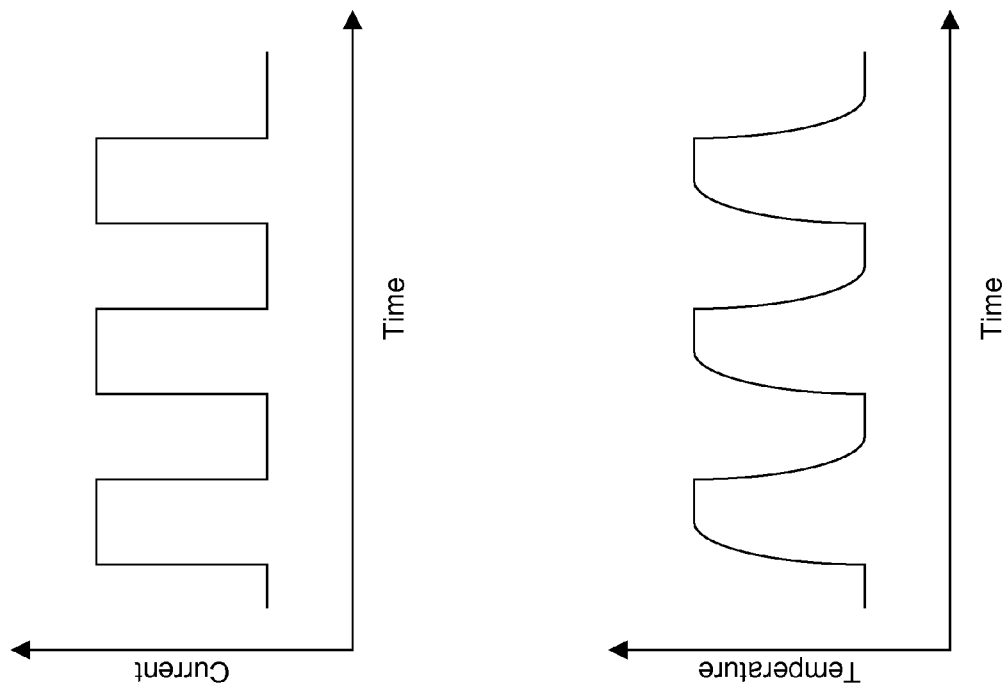
FIGS. 10A and 10B depict schemes from controlling the flow of current through a platen according to one embodiment of the invention.
Figure 10A:
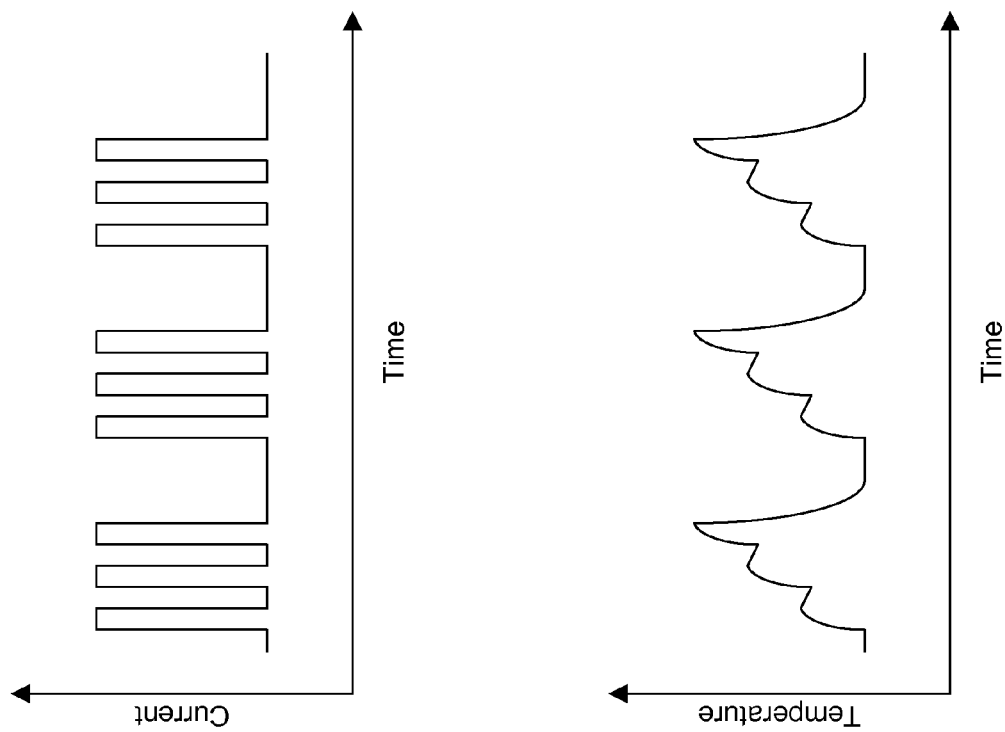

Various schemes are possible for feedback control of the current through the platen 906 based on modulation of the frequency and time duration of the opening and closing of the switch. One scheme depicted in FIG. 10A is pulse modulation as it enables simplified and precise control of the array temperature by changing the frequency of current pulses through the platen 906. If there is a large difference between the array 202 and set point temperature, the pulse frequency is high, driving more current on average through the platen. As the temperature difference decreases, so does the pulse frequency, ultimately reaching zero when the set point temperature is reached. This control scheme is amendable to low power switching power supply electronics. An alternative scheme depicted in FIG. 10B is to have a fixed pulse frequency but vary the time duration of the current pulses in proportion with the difference between the thermal sensor and set point temperatures—the larger the temperature difference, the longer the current pulse duration.

Figure 11A:
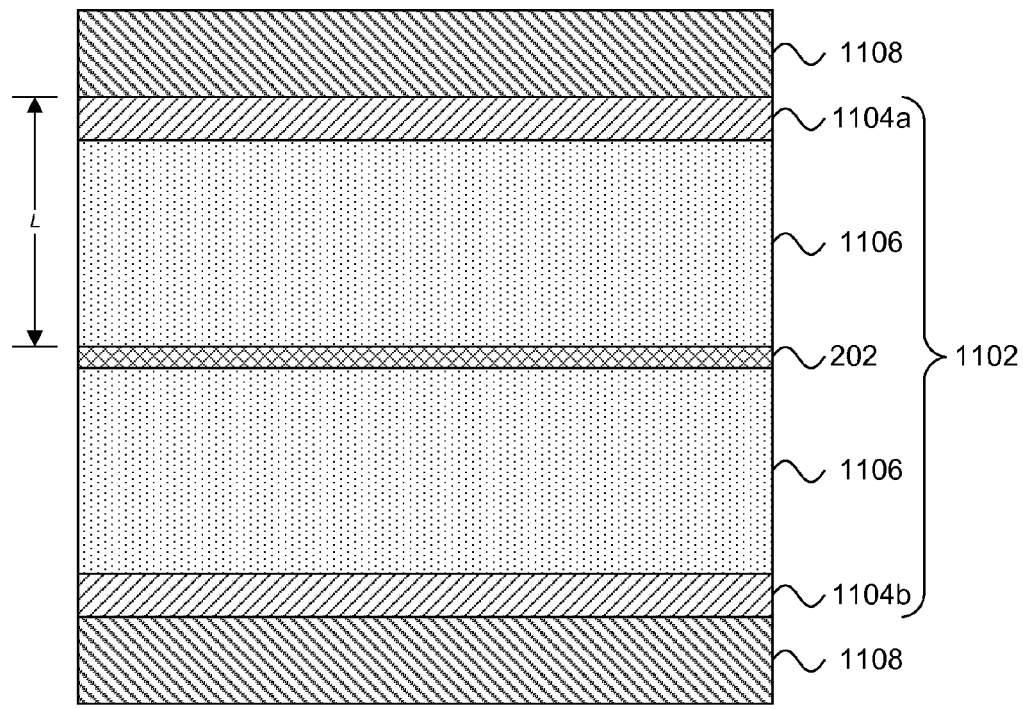
FIGS. 11A and 11B illustrate a one-dimensional thermal model for estimating the temperature decrease of a platen during Joule heating by a current pulse according to one embodiment of the invention.
Figure 11B:
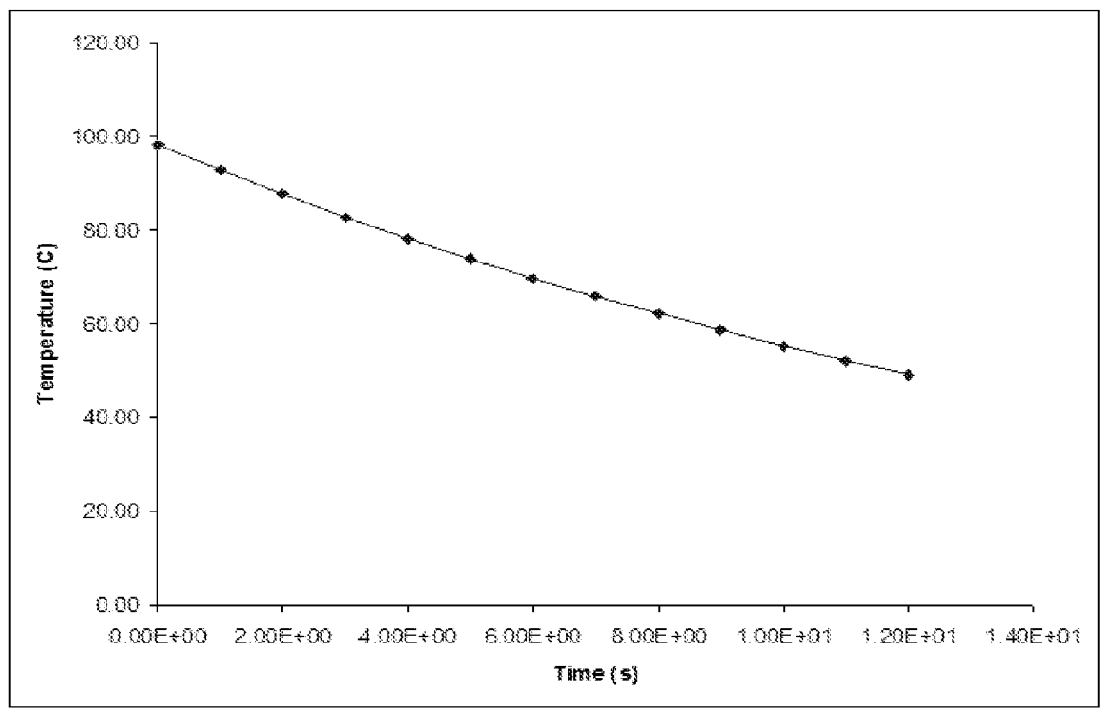

FIG. 11A provides a one-dimensional thermal model for estimating the temperature decrease of the platen 202 during Joule heating by a current pulse. It is assumed that the platen is heated instantaneously (relative to the heat loss) when current is injected into the platen. The thermophysical parameters of an exemplary soda lime glass case 1104a, 1104b and FLUORINERT® FC-77 coolant 1106 are depicted below:

| Parameter | FC-77 | Glass |
|---|---|---|
| Thermal conductivity (k) | $0.057 \frac{W}{m \cdot K}$ | $1.05 \frac{W}{m \cdot K}$ |
| Specific heat (c) | $1172 \frac{J}{kg \cdot K}$ | $840 \frac{J}{kg \cdot K}$ |
| Density (ρ) | $1780 \frac{kg}{m^3}$ | $2500 \frac{kg}{m^3}$ |

It is assumed that the specific heat of the platen material (e.g. 317 stainelss steel) is substantially lower (e.g. by over an order of magnitude) while the thermal conductivity of the platent material is substantially higher (e.g. by over an order of magnitude) and that these parameters do not significantly impact the rate of heat loss from the platen.

FIG. 11A depicts a cross section of an exemplary case 1102 enclosing a platen 202 between two layers of soda lime glass 1104a, 1104b and FLUORINERT® FC-77 (1106). The case is immersed in a liquid heat sink 1108 as described herein held at a constant temperature ($T_{sink}$).

The following thermal model is derived based on the above assumptions and describes the time dependence of the temperature difference between the platen 202 and the heat sink 1108 when a pulse of current (i) heats the platen 202 by Joule heating:

$$T = T_{sink} + \frac{i^2 R \cdot \Delta t}{m \cdot c} e^{\frac{-2k}{\rho \cdot c \cdot L^2} t}$$

In the above model, $T_{sink}$ is the temperature of the heat sink, i is the input current, R is the platen resistance, Δt is the pulse duration, m is the mass of the FC-77 fluid and the glass, c is the specific heat of the FC-77 fluid and the glass, k is the thermal conductivity of the FC-77 fluid and the glass, p is the density of the FC-77 fluid and the glass, and L is the thickness of the FC-77 fluid and the glass.

Assuming a current pulse amplitude of 200 A in one second pulses through a platen of 10 mΩ resistance and combined FC-77 fluid and glass slide thickness of one millimeter, the platen 202 will reach an initial double-stranded DNA target melting temperature (FIG. 6d) of 98.26° C. and decrease to an annealing temperature of 55° C. in ten seconds. The ramp up back to the melting temperature is assumed to take less than one second. Based on these assumptions, a 40-cycle PCR protocol will take approximately 440 seconds or 7.3 minutes—substantially faster than conventional flat block thermal cycler where heat is conducted through the material comprising the walls of the liquid container to heat the liquid and back out again to cool the liquid. The approach proposed here is fundamentally different in that the container itself is directly heated to then heat the enclosed liquid by thermal conduction. Heat is removed from the reaction volume by conduction through the platen 202 and encapsulating liquid 1106 and glass slides 1104a, 1104b to the external heat sink 1108.

In another example, again assume that the plate has a resistance of 10 mΩ and that the dominant thermal loss is through the FC-77 liquid. A current pulse of 500 A and 5 V applied to the plate for 150 ms will heat the plate to 95.87° C. The average power of into the plate is 375 W (5 V×500 A×0.15 s), which can be provide by a standard pulsed power supply (e.g. a power supply from standard photographic strobe flash devices).

Compensation for Spatially Non-Uniform Heating

Injection and extraction of thermal energy to ensure spatially uniform heating and cooling of the fluidic array is important for uniform PCR amplification. Typically, if the cassette is heated and cooled on a flat thermal cycler block, the higher thermal conductivity of the polymer spacer relative to the FLUORINERT® liquid and the intimate thermal contact between the case spacer and the metal array relative to the FLUORINERT® liquid in contact with the array causes the temperature at the edges of the array to lead the temperature change at the center of the array. This temperature gradient across the array can be as large as 1-2° C. while the package is heated or cooled.

One approach to minimizing this thermal gradient is to differentially heat/cool the thermal package such that the heat flux is greater in the center of the array compared with the edges. This strategy is readily accommodated in the present embodiment by electrically segmenting the conductive plate such that there is a slightly greater electrical current through the central region of the plate than along its edges. In turn, the plate temperature mirrors the spatial distribution of electrical current through the plate.

Figure 12:
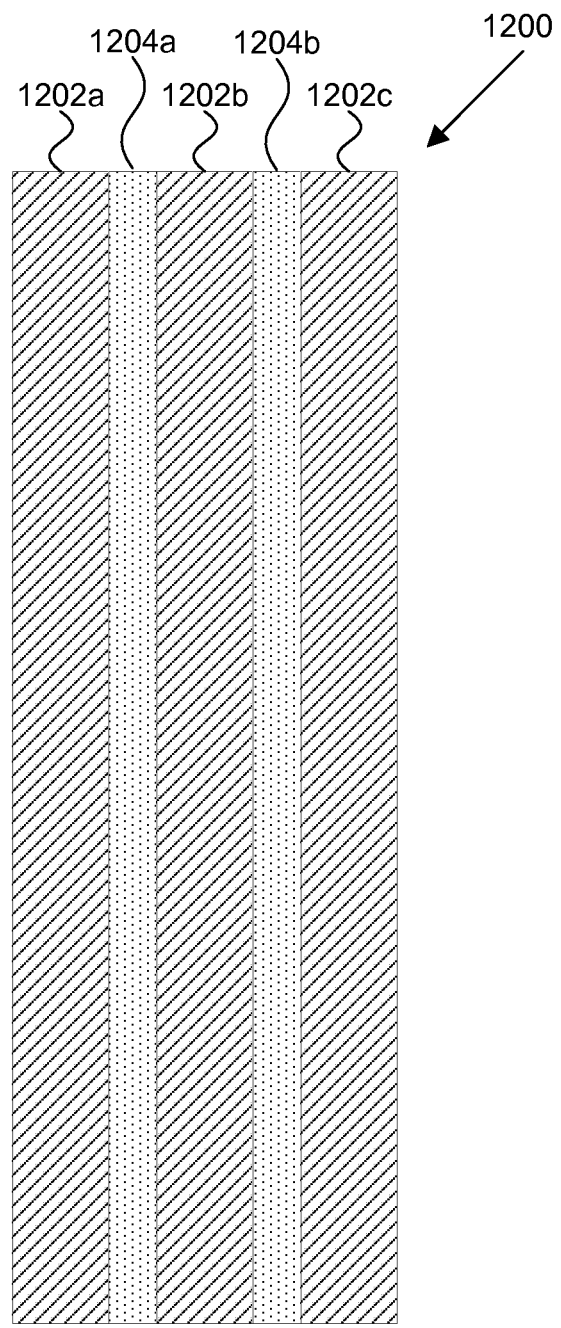
FIG. 12 depicts a case containing three conductive strips according to one embodiment of the invention.

An exemplary case 1200 is depicted in FIG. 12. The conductive portion of case 1200 includes three conductive strips 1202a, 1202b, 1202c separated by two regions 1204a, 1204b of electrically and thermally insulating material. The insulating material can be an adhesive, air, or an insulating liquid, depending on the positioning of the conductive strips within the case 1200 A different current through each strip 1202a, 1202b, 1202c is achieved by allowing each strip 1202a, 1202b, 1202c to have a different intrinsic resistance than its neighbors or by changing the resistance with external resistors between the strips 1202a, 1202b, 1202c and current supply.

For example, if external resistors are used, an infrared sensitive camera can be used to image the array 202 with equal value resistors to establish a temperature baseline as the plate is heated and cooled. The resistor values can then be changed to minimize the observed temperature gradient across the array 202 as the temperature changes. Because the power dissipated is proportional to electrical resistance, and the observed temperature gradient is proportional to the spatial distribution of dissipated power, small changes in the external resistor can decrease the temperature difference across the plate.

Direct Heating of the Through-Hole Array

In another embodiment, the through-hole array is directly heated by passing an electrical current through the array substrate itself. As shown in FIG. 3, case 200 can be modified by inclusion of an electrode 312 such that the array 202 makes electrical contact with the electrode 312 on insertion into the case 200. The plug of UV curable epoxy can be replaced with a mechanical plug 314 providing an electrical contact to the array 202. The case 200 can be held vertically to prevent the liquid from leaking from the case. The electrodes 312, 314 embedded in the case 200 package provide the connection to the external current supply 304a, 304b and electrical switch 306. A temperature sensor in intimate thermal contact with the array 202 can provide temperature information for feedback control of injection of the electrical current into the array 202. Control schemes such as those described herein can be applied to control the array temperature. Because of the potential for electrical interference with the thermal sensor, the sensor can, in some embodiments, be read-out only between current pulses applied to the array 202.

The case 200 can be placed on a constant temperature heat sink at a temperature substantially less than the PCR annealing temperature to cool the array after heating. The rate of cooling is directly proportional to the difference in temperature between the block and the lowest temperature of the PCR process. Since the annealing temperature is typically between 50-60° C., a heat sink of lower temperature is typical.

Heating of Through-Hole Arrays by Radio Frequency (RF)

In another embodiment of the invention, the through-hole array is heated via radio waves (e.g. microwaves). In such an embodiment, the case 200 can be fabricated from dielectric, non-conductive materials, while the through-hole array 202 is formed from conductive materials. Suitable RF heating frequencies include frequencies between about 0.1 MHz and about 10 MHz.

The heating of through-hole arrays can be controlled according to the control schemes described herein. The cooling of through-hole arrays can be effected by a variety heat sinks as described herein.

Heating of Through-Hole Arrays by Infrared Waves

In another embodiment, the samples inside the through-holes are directly and/or selectively heated using near-IR radiation. Water is a strong absorber of near-IR radiation around 1050 nm, whereas FC-77 liquid and other perfluorinated hydrorcarbon oils are highly transmissive in the near-infrared region. The near-IR radiation is provided by an infrared LED array or other narrowband IR radiation source located on the opposite side of the array from the CCD camera. Cooling is provided by circulating chilled perfluorinated hydrorcarbon oils around the sample.

Thermal Cycling of Through-Hole Array Through Direct Contact with Liquids

In another embodiment, the heating and cooling of the samples in a through-hole array is caused by alternating the flow of hot and cold immiscible liquid into a chamber containing the OPENARRAY™ device. In some embodiment, the chamber is a variant of the through-hole array cases described herein.

Figure 13:
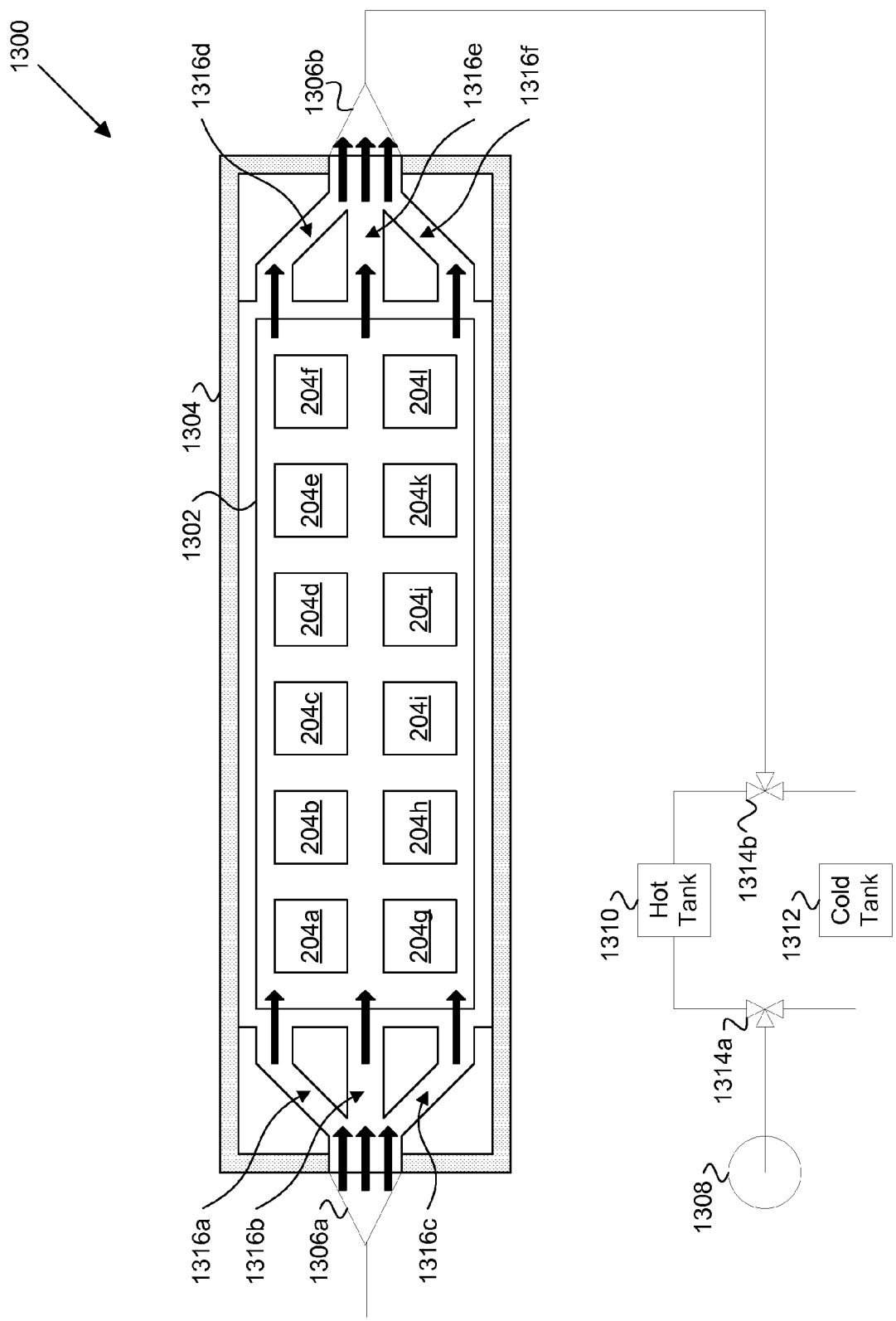
FIG. 13 depicts a system for thermal cycling a through-hole array according to one embodiment of the invention.

FIG. 13 depicts an exemplary embodiment of a system 1300 for thermal cycling a through-hole array 1302. The system includes a case 1304 for receiving the through-hole array 1302. The case 1304 includes a first port 1306a located at a first end of the case 1304 and a second port 1306b located at a second end of the case 1304. Ports 1306a, 1306b are connected to a fluidic circuit including a pump 1308, a hot tank 1310, and a cold tank 1312. Valves 1314a, 1314b are selectively actuated to allow for the alternative flow of hot fluid and cold fluid through the case 1304.

The case 1304 can include a plurality of veins 1316a-f to promote a more uniform flow rate over the through-hole array 1302. In some embodiments, the samples are protected by first covering the through-hole array 1302 in a thin layer of an inert oil that is immiscible to the liquid used to heat and cool the through-hole array 1302.

Heat Sinks

A variety of heat sinks can be used to cool the through-hole arrays and cases provided herein. For example, the heat sink can be a cooled block composed of a thermally-conductive material such as a metal. The block can be passively cooled or actively cooled by flowing air or liquid through channels or veins located within or on a surface of the block. Additionally or alternatively, the block can be or can be coupled with a Peltier cooling element.

The heat sink can additionally or alternatively be a fluid bath containing, for example, a liquid or an ice slurry. The fluid bath can be a stationary bath or can be circulated, e.g. through a refrigerator pump.

The heat sink can also be a gas stream directed over case 200. For example, one or more fans or jets can be arranged to flow a cool stream of a gas over the case. The gas can be, e.g., air or liquid nitrogen.

The case can be in continuous contact with the heat sink or contact can be variable. For example, the case 200 can be completely removed from the heat sink (e.g. by lifting the case out of a fluid bath) when the array is heated. Alternatively, the fluid bath or gas stream can be circulated when the case 200 is cooled and not circulated when the case 200 is heated.

Methods of Thermal Cycling

Figure 14:
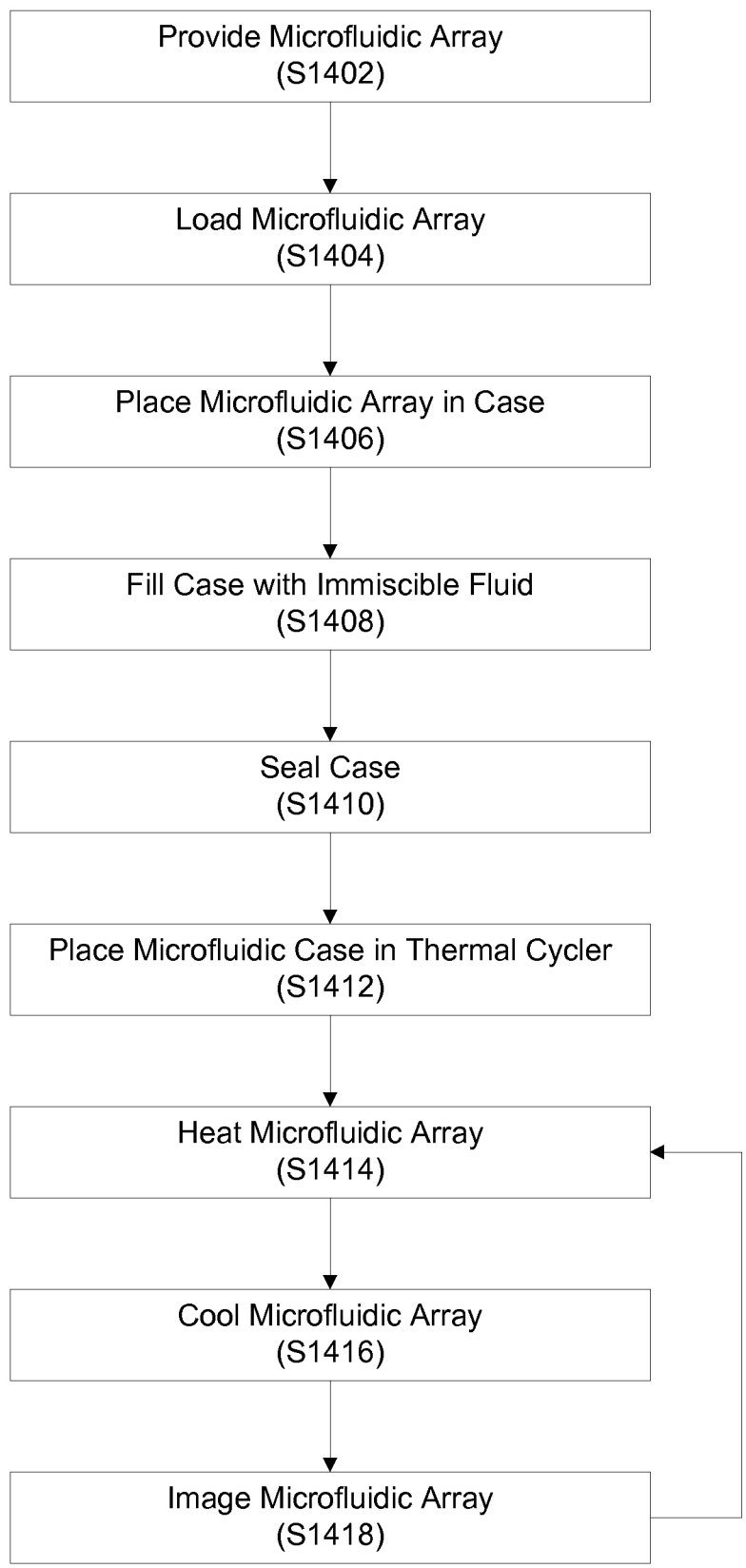
FIG. 14 depicts a method for thermal cycling a plurality of samples according to one embodiment of the invention.

As described herein, the devices herein can be used for a variety of thermal cycling methods. An exemplary embodiment is depicted in FIG. 14.

In step S1402, a microfluidic array is provided. The microfluidic array can in some embodiments be a through-hole array as described herein. However, other microfluidic devices can be used including glass, plastic, metal, or silicon plates containing a plurality of microwells etched in a surface, but not extending to an opposing surface.

In step S1404, the microfluidic array is loaded. The microfluidic array can be loaded by a variety of known methods including dip loading, droplet dragging, and the use of one or more pipettes. Various microfluidic array loading techniques are described in U.S. Pat. Nos. 6,306,578; 6,387,331; 6,436,632; 6,716,629; 6,743,633; 6,893,877; 7,332,271; and U.S. Patent Application Publication Nos. 2001/0055765; 2002/0151040; 2002/0192716; 2003/0124716; 2003/0180804; 2004/0037748; 2004/0171166; 2004/0191924; 2004/0208792; 2005/0059074; 2005/0079105; 2005/0148066; 2005/0230213; 2006/0183171; 2007/0003448; and 2008/0108112. Suitable devices for loading microfluidic arrays include the OPENARRAY® AUTOLOADER™ device available from BioTrove, Inc. of Woburn, Mass.

In steps S1406, the microfluidic array is placed in an appropriate case. In step S1408, the case is filled with an immiscible fluid (e.g. FLUORINERT® FC-77 fluid). The case is then sealed in step S1410. For example, the case can be sealed inserting a mechanical plug or applying an adhesive to fill an opening in the case or bond one or more walls of the case. The adhesive can be a UV-curable adhesive as discussed herein and in U.S. Patent Application Publication No. 2004/0208792.

In step S1412, the case is placed in a thermal cycler. The case can be positioned to mate with a particular thermal cycler geometry. For example, one or more electrical contacts on an exterior surface of the case can be aligned with corresponding contacts in the thermal cycler. Alternatively, one or more ports on a case can be coupled with outlets for a fluidic circuit in the thermal cycler. The thermal cycler can, in some embodiments, include one or more clamps or locks to hold the case against electrical contacts and/or the heat sink. Suitable clamps include one or more fingers described in U.S. Patent Application Publication No. 2006/0094108. Such fingers advantageously apply pressure to the case without obstructing imaging of the array through a transparent wall of the case.

In step S1414, the microfluidic array is heated. This heating can be accomplished by a variety of methods as described herein including: Joule heating of the case, Joule heating of the microfluidic array, infrared heating, radiation heating, and flowing heating fluid through the case. The microfluidic array is heated to a desired temperature (e.g. 98.26° C.—the melting temperature for double-stranded DNA).

In step S1416, the microfluidic array is cooled. This cooling can be accomplished by a variety of method as described herein including: removing a heat source, exposing the case to ambient air, exposing the case to chilled liquid, placing the case in contact with a chilled surface, flowing a chilled liquid through the case. The microfluidic array is heated to a desired temperature (e.g. 55° C.—the annealing temperature for double-stranded DNA).

In step S1418, the microfluidic array is optionally imaged. The imaging can be in accordance with real-time PCR method as described in U.S. Pat. Nos. 6,814,934; 7,188,030; 7,228,237; and 7,272,506. The heating, cooling, and imaging steps can be repeated.

EQUIVALENTS

The foregoing specification and the drawings forming part hereof are illustrative in nature and demonstrate certain preferred embodiments of the invention. It should be recognized and understood, however, that the description is not to be construed as limiting of the invention because many changes, modifications and variations may be made therein by those of skill in the art without departing from the essential scope, spirit or intention of the invention. Also, various combinations of elements, steps, features, and/or aspects of the described embodiments are possible and contemplated even if such combinations are not expressly identified herein.

INCORPORATION BY REFERENCE

The entire contents of all patents, published patent applications, and other references cited herein are hereby expressly incorporated herein in their entireties by reference.

What is claimed is:

1. A through-hole array comprising:
  a platen comprising:
    a first external planar surface having a two-dimensional array of first openings;
    a second external planar surface opposite the first planar surface, the second external planar surface having a two-dimensional array of second openings; and
    a plurality of through-holes extending between the surfaces from each of the first openings to a corresponding one of the second openings;
  a plurality of strips, the plurality of through-holes located on one or more of the plurality of strips; and
  a plurality of electrically conductive fingers in contact with corresponding ones of the plurality of strips, the electrically conductive fingers configured to direct electrical current through the strips.

2. The through-hole array of claim 1, wherein the strips are substantially parallel.

3. The through-hole array of claim 1, further comprising:
  one or more slots, each slot separating two of the plurality of strips.

4. The through-hole array of claim 1, wherein the platen is formed from a conductive material.

5. The through-hole array of claim 4, wherein the conductive material selected from the group consisting of: copper, gold, silver, nickel, iron, titanium, steel, and stainless steel.

6. The through-hole array of claim 1, wherein the plurality of through-holes located on one of the plurality of strips are arranged in a single column.

7. The through-hole array of claim 1, wherein the through-holes have a hydrophilic interior.

8. The through-hole array of claim 1, further comprising: two outer layers of hydrophobic material coupled to a top and a bottom surface of the plurality of the strips.

9. The through-hole array of claim 1, wherein each of the plurality of through-holes has a volume less than 100 nanoliters.

10. A through-hole array comprising:
a platen comprising:
   a first external planar surface having a two-dimensional array of first openings arranged in rows of openings disposed along a line;
   a second external planar surface opposite the first planar surface, the second external planar surface having a two-dimensional array of second openings; and
   a plurality of through-holes extending from each of the first openings to a corresponding one of the second openings; and
a plurality of pairs of electrically conductive fingers, each pair of fingers disposed at opposite ends per row, said fingers providing electrical current through a single row in the array.

11. The through-hole array of claim 10, wherein the platen is formed from a conductive material.

12. The through-hole array of claim 11, wherein the conductive material selected from the group consisting of: copper, gold, silver, nickel, iron, titanium, steel, and stainless steel.

13. The through-hole array of claim 10, wherein the through-holes have a hydrophilic interior.

14. The through-hole array of claim 10, wherein each of the plurality of through-holes has a volume less than 100 nanoliters.

* * * * *